United States Patent
Høgset

(10) Patent No.: US 11,027,017 B2
(45) Date of Patent: Jun. 8, 2021

(54) PCI METHOD FOR GENERATING IMMUNE RESPOSE TO ANTIGENIC MOLECULE USING CHECKPOINT INHIBITOR AND TLR3 LIGAND

(71) Applicant: PCI Biotech AS, Oslo (NO)

(72) Inventor: Anders Høgset, Oslo (NO)

(73) Assignee: PCI Biotech AS, Oslo (NO)

( * ) Notice: Subject to any disclaimer, the term of this patent is extended or adjusted under 35 U.S.C. 154(b) by 51 days.

(21) Appl. No.: 15/555,205

(22) PCT Filed: Mar. 4, 2016

(86) PCT No.: PCT/EP2016/054714
§ 371 (c)(1),
(2) Date: Sep. 1, 2017

(87) PCT Pub. No.: WO2016/139362
PCT Pub. Date: Sep. 9, 2016

(65) Prior Publication Data
US 2018/0050105 A1    Feb. 22, 2018

(30) Foreign Application Priority Data
Mar. 5, 2015 (GB) .................................. 1503776.5

(51) Int. Cl.
| | |
|---|---|
| *A61K 39/00* | (2006.01) |
| *C12N 5/09* | (2010.01) |
| *A61N 5/06* | (2006.01) |
| *A61K 41/00* | (2020.01) |
| *A61K 39/12* | (2006.01) |
| *A61K 39/39* | (2006.01) |
| *A61K 47/69* | (2017.01) |
| *A61K 39/395* | (2006.01) |
| *C07K 16/28* | (2006.01) |
| *A61K 9/00* | (2006.01) |
| *A61K 31/713* | (2006.01) |
| *A61K 35/17* | (2015.01) |
| *C12N 5/0784* | (2010.01) |
| *C12N 5/0786* | (2010.01) |
| *C12N 7/00* | (2006.01) |
| *C12N 13/00* | (2006.01) |

(52) U.S. Cl.
CPC ........ *A61K 41/0057* (2013.01); *A61K 9/0019* (2013.01); *A61K 31/713* (2013.01); *A61K 35/17* (2013.01); *A61K 39/0011* (2013.01); *A61K 39/12* (2013.01); *A61K 39/39* (2013.01); *A61K 39/3955* (2013.01); *A61K 39/39541* (2013.01); *A61K 41/00* (2013.01); *A61K 47/6901* (2017.08); *C07K 16/2818* (2013.01); *C12N 5/0639* (2013.01); *C12N 5/0645* (2013.01); *C12N 7/00* (2013.01); *C12N 13/00* (2013.01); *A61K 2039/505* (2013.01); *A61K 2039/507* (2013.01); *A61K 2039/5158* (2013.01); *A61K 2039/545* (2013.01); *A61K 2039/55561* (2013.01); *A61K 2039/575* (2013.01); *A61K 2039/585* (2013.01); *C07K 2317/76* (2013.01); *C12N 2501/50* (2013.01); *C12N 2501/599* (2013.01); *C12N 2502/1114* (2013.01); *C12N 2710/20034* (2013.01); *C12N 2710/20071* (2013.01)

(58) Field of Classification Search
None
See application file for complete search history.

(56) References Cited

U.S. PATENT DOCUMENTS

| | | | | |
|---|---|---|---|---|
| 9,737,594 B2 * | 8/2017 | Berg | ................ | A61K 39/0011 |
| 10,011,656 B2 * | 7/2018 | Freeman | ............ | C07K 16/2818 |
| 2012/0253264 A1 * | 10/2012 | Klaveness | ............ | A61K 9/0014 604/20 |
| 2016/0206725 A1 * | 7/2016 | Hogset | ................ | A61K 39/0011 |
| 2016/0257753 A1 * | 9/2016 | Korman | ............ | A01K 67/0275 |

FOREIGN PATENT DOCUMENTS

| | | |
|---|---|---|
| CN | 1633598 | 6/2005 |
| GB | 2 420 784 | 6/2006 |
| WO | 96/07432 | 3/1996 |
| WO | 00/54802 | 9/2000 |
| WO | 02/44395 | 6/2002 |
| WO | 02/44396 | 6/2002 |
| WO | 03/020309 | 3/2003 |
| WO | 03/031573 | 4/2003 |
| WO | 2008/007073 | 1/2008 |
| WO | 2011/018635 | 2/2011 |

(Continued)

OTHER PUBLICATIONS

Zhu et al ( J of Clinical Investigation, 2010, v.120, pp. 607-616).*
Parvizi et al ( Viral Immunol, 2012,v.25 pp. 394-401).*
Håkerud et al., "Photosensitisation facilitates cross-priming of adjuvant-free protein vaccines and stimulation of tumour-suppressing CD8 T cells", Journal of Controlled Release, 198: 10-17 (2015).

(Continued)

*Primary Examiner* — Michail A Belyavskyi
(74) *Attorney, Agent, or Firm* — Wenderoth, Lind & Ponack, L.L.P.

(57) ABSTRACT

The invention concerns a method of generating an immune response in a subject, comprising administering to the subject an antigenic molecule, a photosensitizing agent, a checkpoint inhibitor, and irradiating said subject with light of a wavelength effective to activate the photosensitizing agent to generate an immune response. Preferably the method is a method of vaccination. The invention also provides related methods, compositions, cells, uses, products and kits.

11 Claims, 8 Drawing Sheets
Specification includes a Sequence Listing.

(56) References Cited

FOREIGN PATENT DOCUMENTS

| WO | 2011/018636 | | 2/2011 |
|---|---|---|---|
| WO | 2013/106852 | | 7/2013 |
| WO | 2013/189663 | | 12/2013 |
| WO | 2014/139597 | | 9/2014 |
| WO | 2015/028574 | | 3/2015 |
| WO | WO2016089950 | * | 6/2016 |

OTHER PUBLICATIONS

Callahan et al., "CTLA-4 and PD-1 pathway blockade: combinations in the clinic", Frontiers in Oncology, 4: 1-6 (2015).

International Search Report and Written Opinion of the International Searching Authority, dated Jun. 28, 2016 in corresponding International application No. PCT/EP2016/054714.

Office Action dated Oct. 8, 2020 in corresponding Brazilian Patent Application No. BR112017018948-8 with English-language translation.

Sun, W. et al. Medical Immunology, pp. 126-129, Beijing: Higher Education Press, Jan. 31, 2013 with English language.

Office Action dated Aug. 5, 2020, in corresponding Chinese Patent Application No. 201680023471.1 with English-language translation.

Håkerud et al., "Intradermal photosensitisation facilitates stimulation of MHC class-I restricted CD8 T-cell responses of co-administered antigen", 2014, J. Controlled Release, vol. 174, p143-150.

McArdle et al., "Tenth International Conference on Progress in Vaccination Against Cancer (PIVAC 10), Cambridge, UK, Sep. 27-30, 2010: New hopes and strategies for cancer vaccines", 2011, Cancer Immunology Immunotherapy, vol. 60 (8), pp. 1207-1210.

Schlom, "Therapeutic Cancer Vaccines: Current Status and Moving Forward", 2012, Journal of National Cancer Institute, vol. 104(8), pp. 599-613.

Berg and Moan, "Lysosomes and Microtubules as Targets for Photochemotherapy of Cancer", 1997, J. Photochemistry and Photobiology, 65, 403-409.

Creelan, "Update on Immune Checkpoint Inhibitors in Lung Cancer", 2014, Cancer Control 21:80-89.

Nagato et al., "Combinatorial Immunotherapy of Polyinosinic-Polycytidylic Acid and Blockade of Programmed Death-Ligand I Induce Effective CD8 T-cell Responses againsts Established Tumors", 2014 Clinical Cancer Research, vol. 20 (5), pp. 1223-1234.

Soliman and Nelson, "Combination immunotherapy with PD-L1 blockade and Poly I:C in a murine breast cancer model", 2014, Cancer Research, vol. 74, No. 19 supplement, Abstract No. 5018.

Bald et al., "Immune Cell-Poor Melanomas Benefit from PD-1 Blockade after Targeted Type I IFN Activation", 2014, Cancer Discovery, vol. 4(6), pp. 674-687.

Weck et al., "TLR ligands differentially affect uptake and presentation of cellular antigens", 2007, Blood, vol. 109(9), pp. 3890-3894.

Berg et al., "Disulfonated tetraphenyl chlorin (TPCS2a), a novel photosensitizer developed for clinical utilization of photochemical internalization", 2011, Photochem. Photobiol. Sci., vol. 10, pp. 1637-1651.

Blasius & Beutler, "Intracellular Toll-like Receptors", 2010, Immunity, vol. 32, pp. 305-315.

Cheng & Xu, "Anticancer function of polyinosinic-polycytidylic acid" 2010, Cancer Biology and Therapy, vol. 10(12), pp. 1219-1223.

Wesch et al., "Modulation of γδ T cell responses by TLR ligands", 2011, Cell. Mol. Life Sci., vol. 68, pp. 2357-2370.

Baglo et al., "Enhanced Efficacy of Bleomycin in Bladder Cancer Cells by Photocemical Internalization", 2014, Biomed Research International, vol. 77(3), p. 759-10.

Folini et al., "Photochemical Internalization of a Peptide Nucleic Acid Targeting the Catalytic Subunit of Human Telomerase", 2003, Cancer Research, vol. 63(13), pp. 3490-3494.

Selbo et al., "Photochemical Internalization of Therapeutic Macromolecular Agents: A Novel Strategy to Kill Multidrug-Resistant Cancer Cells", 2006, J. Pharmacology and Experimental Therapeutics, vol. 319(2), pp. 604-612.

Selbo et al., "Multi-Modality Therapeutics with Potent Anti-Tumor Effects: Photochemical Internalization Enhances Delivery of the Fusion Toxin scFvMEL/rGel", 2009, PLOS One, vol. 4(8), e6691.

* cited by examiner

PCI METHOD FOR GENERATING IMMUNE RESPOSE TO ANTIGENIC MOLECULE USING CHECKPOINT INHIBITOR AND TLR3 LIGAND

The present invention relates to a method of vaccination or immunisation involving the use of a photosensitizing agent, an antigenic molecule, e.g. a vaccine component, a checkpoint inhibitor as defined herein (and optionally a ligand for a Toll-like receptor (TLR)), and irradiation with light of a wavelength effective to activate the photosensitizing agent. The invention also relates to antigenic, e.g. vaccine compositions, useful in such a method. The invention also provides a method of generating antigen presenting cells which may be used to generate an immune response, e.g. for vaccination, which involves using the same components as above to introduce antigenic molecules, e.g. vaccine components, into cells to achieve antigen presentation, and to antigenic compositions useful in such a method. The invention also provides use of cells generated in vitro by such methods for administration to a patient in vivo to elicit an immune response, e.g. to achieve vaccination. A method of internalising an antigenic molecule into a cell is also provided.

Vaccination involves administration of antigenic molecules to provoke the immune system to stimulate development of an adaptive immunity to a pathogen. Vaccines can prevent or improve morbidity from infection. Vaccination is the most effective method of preventing infectious diseases, and widespread immunity due to vaccination is largely responsible for the worldwide eradication of smallpox and the restriction of diseases such as polio, measles, and tetanus from much of the world.

The active agent of a vaccine may be intact but inactivated (non-infective) or attenuated (with reduced infectivity) forms of the causative pathogens, or purified components of the pathogen that have been found to be immunogenic (e.g., outer coat proteins of a virus). Toxoids are produced for immunization against toxin-based diseases, such as the modification of tetanospasmin toxin of tetanus to remove its toxic effect but retain its immunogenic effect.

Since most vaccines are taken up by antigen presenting cells through endocytosis and transported via endosomes to lysosomes for antigen digestion and presentation via the MHC class-II pathway, vaccination primarily activates CD4 T-helper cells and B cells. To combat disorders or diseases such as cancer, as well as intracellular infections, the stimulation of cytotoxic CD8 T-cell responses is important. However, the induction of cytotoxic CD8 T cells usually fails due to the difficulty in delivering antigen to the cytosol and to the MHC class-I pathway of antigen presentation. Photochemical internalisation (PCI) improves delivery of molecules into the cytosol and methods of vaccination which employ PCI are known. PCI is a technique which uses a photosensitizing agent, in combination with an irradiation step to activate that agent, and is known to achieve release of molecules co-administered to a cell into the cell's cytosol. This technique allows molecules that are taken up by the cell into organelles, such as endosomes, to be released from these organelles into the cytosol, following irradiation. PCI provides a mechanism for introducing otherwise membrane-impermeable (or poorly permeable) molecules into the cytosol of a cell in a manner which does not result in widespread cell destruction or cell death.

The basic method of photochemical internalisation (PCI), is described in WO 96/07432 and WO 00/54802, which are incorporated herein by reference. In such methods, the molecule to be internalised (which in the present invention would be the antigenic molecule), and a photosensitizing agent are brought into contact with a cell. The photosensitizing agent and the molecule to be internalised are taken up into a cellular membrane-bound subcompartment within the cell, i.e. they are endocytosed into an intracellular vesicle (e.g. a lysosome or endosome). On exposure of the cell to light of the appropriate wavelength, the photosensitizing agent is activated which directly or indirectly generates reactive species which disrupt the intracellular vesicle's membranes. This allows the internalized molecule to be released into the cytosol.

It was found that in such a method the functionality or the viability of the majority of the cells was not deleteriously affected. Thus, the utility of such a method, termed "photochemical internalisation" was proposed for transporting a variety of different molecules, including therapeutic agents, into the cytosol i.e. into the interior of a cell.

WO 00/54802 utilises such a general method to present or express transfer molecules on a cell surface. Thus, following transport and release of a molecule into the cell cytosol, it (or a part of that molecule) may be transported to the surface of the cell where it may be presented on the outside of the cell i.e. on the cell surface. Such a method has particular utility in the field of vaccination, where vaccine components i.e. antigens or immunogens, may be introduced to a cell for presentation on the surface of that cell, in order to induce, facilitate or augment an immune response.

Whilst vaccination has achieved some noteworthy successes, there remains a need for alternative and improved vaccination methods. The present invention addresses this need.

The present inventors have surprisingly found that, advantageously, a method involving the use of a photosensitizing agent, an antigenic molecule, e.g. a vaccine component, and a checkpoint inhibitor (and optionally a TLR ligand) as defined herein, and irradiation with light of a wavelength effective to activate the photosensitizing agent results in improved vaccination or an improved immune response.

As will be described in more detail in the Examples below, it has been demonstrated that the method of the invention results in improved vaccination or an improved immune response, e.g. production of an increased amount of antigen-specific T cells. In addition, the Examples show that, in the context of cancer vaccination, a method according to the invention leads to a decrease in tumour volume.

Whilst not wishing to be bound by theory, it is believed that the methods of the invention result in increased antigen presentation on MHC Class I molecules leading to an increased CD8+ T cell responses and hence improved vaccination methods.

The results with the methods of the present invention show increased numbers of antigen-specific T cells, and increased TNF-α and IFNγ production by the T cells, which is correlated with increased or improved antigen presentation.

Thus, in a first aspect the present invention provides a method of generating an immune response in a subject, comprising administering to said subject an antigenic molecule, a photosensitizing agent, a checkpoint inhibitor, and irradiating said subject with light of a wavelength effective to activate said photosensitizing agent, wherein an immune response is generated.

In a further aspect the present invention provides a method of expressing an antigenic molecule or a part thereof on the surface of a cell, comprising:

a) providing a first cell on which said antigenic molecule or part thereof is to be expressed and a second cell to which a checkpoint inhibitor may bind, wherein said first and second cell may be the same cell or different cells,
b) contacting at least said first cell with said antigenic molecule, a photosensitizing agent, and optionally a TLR ligand,
c) contacting at least the second cell with a checkpoint inhibitor, and
d) irradiating at least the first cell with light of a wavelength effective to activate the photosensitising agent, wherein said antigenic molecule is released into the cytosol of the cell and the antigenic molecule or a part thereof is subsequently presented on the surface of the first cell,
wherein said first and second cells are contacted with one another before, during and/or after said irradiation.

Preferably these methods (and subsequently described methods) employ only the above described three active ingredients (agents) in said methods and the agents are present at appropriate levels (e.g. at the minimum levels described below) in the methods such that they affect the efficacy of the method (i.e. have an active role in enhancing PCI vaccination/antigen presentation/immune response stimulation). Thus preferably the agents are present in buffers with no other active ingredients. Additionally, agents may, however, be added as described hereinafter, e.g. a TLR ligand.

In such methods said antigenic molecule and said photosensitizing agent, and optionally said checkpoint inhibitor (and optionally said TLR ligand, when used) as defined herein, are each taken up into an intracellular vesicle; and when the cell is irradiated the membrane of the intracellular vesicle is disrupted releasing the antigenic molecule into the cytosol of the cell.

The various agents which are taken up may be taken up into the same or a different intracellular vesicle relative to each other. It has been found that active species produced by photosensitizers may extend beyond the vesicle in which they are contained and/or that vesicles may coalesce allowing the contents of a vesicle to be released by coalescing with a disrupted vesicle. As referred to herein "taken up" signifies that the molecule taken up is wholly contained within the vesicle. The intracellular vesicle is bounded by membranes and may be any such vesicle resulting after endocytosis, e.g. an endosome or lysosome.

As used herein, a "disrupted" compartment refers to destruction of the integrity of the membrane of that compartment either permanently or temporarily, sufficient to allow release of the antigenic molecule contained within it.

A "photosensitizing agent" as referred to herein is a compound that is capable of translating the energy of absorbed light into chemical reactions when the agent is activated on illumination at an appropriate wavelength and intensity to generate an activated species. The highly reactive end products of these processes can result in cyto- and vascular toxicity. Conveniently such a photosensitizing agent may be one which localises to intracellular compartments, particularly endosomes or lysosomes.

Photosensitisers may exert their effects by a variety of mechanisms, directly or indirectly. Thus for example, certain photosensitisers become directly toxic when activated by light, whereas others act to generate toxic species, e.g. oxidising agents such as singlet oxygen or other reactive oxygen species, which are extremely destructive to cellular material and biomolecules such as lipids, proteins and nucleic acids.

A range of such photosensitizing agents are known in the art and are described in the literature, including in WO96/07432, which is incorporated herein by reference, and may be used in method of the invention. There are many known photosensitising agents, including porphyrins, phthalocyanines, purpurins, chlorins, benzoporphyrins, lysomotropic weak bases, naphthalocyanines, cationic dyes and tetracyclines or derivatives thereof (Berg et al., (1997), J. Photochemistry and Photobiology, 65, 403-409). Other photosensitising agents include texaphyrins, pheophorbides, porphycenes, bacteriochlorins, ketochlorins, hematoporphyrin derivatives, and endogenous photosensitizers induced by 5-aminolevulinic acid and derivatives thereof, Photofrin, dimers or other conjugates between photosensitizers.

Porphyrins are the most extensively studied photosensitising agents. Their molecular structure includes four pyrrole rings linked together via methine bridges. They are natural compounds which are often capable of forming metal-complexes. For example in the case of the oxygen transport protein hemoglobin, an iron atom is introduced into the porphyrin core of heme B.

Chlorins are large heterocyclic aromatic rings consisting, at the core, of three pyrroles and one pyrroline coupled through four methine linkages. Unlike porphyrin, a chlorin is therefore largely aromatic, but not aromatic through the entire circumference of the ring.

The skilled man will appreciate which photosensitisers are suitable for use in the present invention. Particularly preferred are photosensitizing agents which locate to endosome or lysosomes of cells. Thus, the photosensitizing agent is preferably an agent which is taken up into the internal compartments of lysosomes or endosomes. Preferably the photosensitizing agent is taken up into intracellular compartments by endocytosis. Preferred photosensitisers are di- and tetrasulfonated aluminium phthalocyanine (e.g. AlPcS$_{2a}$), sulfonated tetraphenylporphines (TPPS$_n$), sulfonated tetraphenyl bacteriochlorins (e.g. TPBS$_{2a}$), nile blue, chlorin e$_6$ derivatives, uroporphyrin I, phylloerythrin, hematoporphyrin and methylene blue. Further appropriate photosensitizers for use in the invention are described in WO03/020309, which is also incorporated herein by reference, namely sulfonated meso-tetraphenyl chlorins, preferably TPCS$_{2a}$. Preferred photosensitizing agents are amphiphilic photosensitizers (e.g. disulfonated photosensitizers) such as amphiphilic phthalocyanines, porphyrins, chlorins and/or bacteriochlorins, and in particular include TPPS$_{2a}$ (tetraphenylporphine disulfonate), AlPcS$_{2a}$ (aluminium phthalocyanine disulfonate), TPCS$_{2a}$ (tetraphenyl chlorin disulfonate) and TPBS$_{2a}$ (tetraphenyl bacteriochlorin disulfonate), or pharmaceutically acceptable salts thereof. Also preferred are hydrophilic photosensitizing agents, for example TPPS$_4$ (meso-tetraphenylporphine tetrasulfonate). Particularly preferred photosensitizing agents are sulfonated aluminium phthalocyanines, sulfonated tetraphenylporphines, sulfonated tetraphenylchlorins and sulfonated tetraphenylbacteriochlorins, preferably TPCS$_{2a}$, AlPcS$_{2a}$, TPPS$_4$ and TPBS$_{2a}$. In a particularly preferred embodiment of the present invention the photosensitizing agent is the chlorin TPCS$_{2a}$ (Disulfonated tetraphenyl chlorin, e.g. Amphinex®).

A photosensitiser may be linked to a carrier to provide the photosensitising agent. Thus, in a preferred aspect of this embodiment of the invention the photosensitising agent is a conjugate of a photosensitiser and chitosan as defined in formula (I):

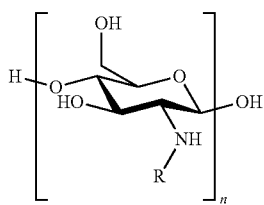
(I)

wherein n is an integer greater than or equal to 3;

R appears n times in said compound, and in 0.1%-99.9% (preferably 0.5%-99.5%) of said total Rn groups, each R is a group A selected from:

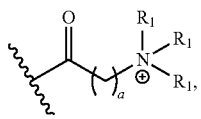

wherein each $R_1$, which may be the same or different, is selected from H, $CH_3$ and $-(CH_2)_b-CH_3$; a is 1, 2, 3, 4 or 5; and b is 0, 1, 2, 3, 4 or 5 (in which the counter-ion may be, for example, $Cl^-$); preferably $R_1$ is $CH_3$ and b is 1, and

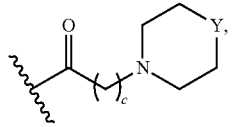

wherein Y is O; S; $SO_2$, $-NCH_3$; or $-N(CH_2)_dCH_3$, c=1, 2, 3, 4 or 5; and d=1, 2, 3, 4 or 5, preferably Y is $NCH_3$ and c is 1, wherein each R group may be the same or different, and in 0.1%-99.9% (preferably 0.5%-99.5%) of said total Rn groups, each R is a group B selected from:

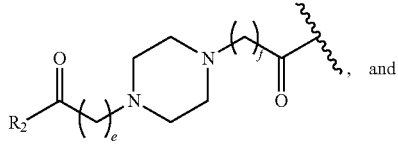, and

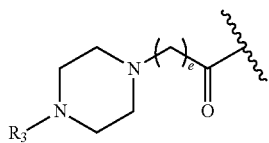

wherein e is 0, 1, 2, 3, 4 or 5; and f is 1, 2, 3, 4 or 5; preferably e and f=1, $R_2$ is a group selected from:

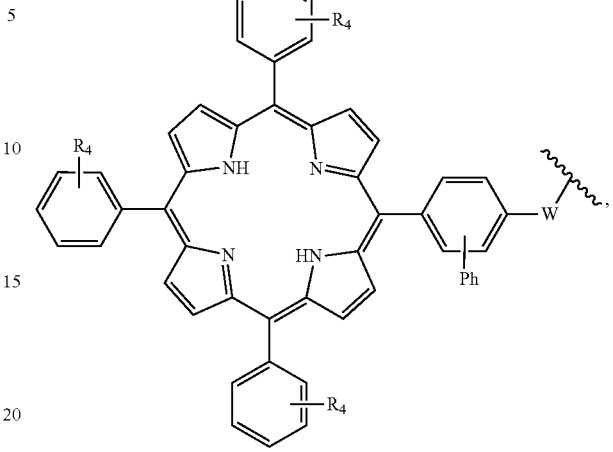

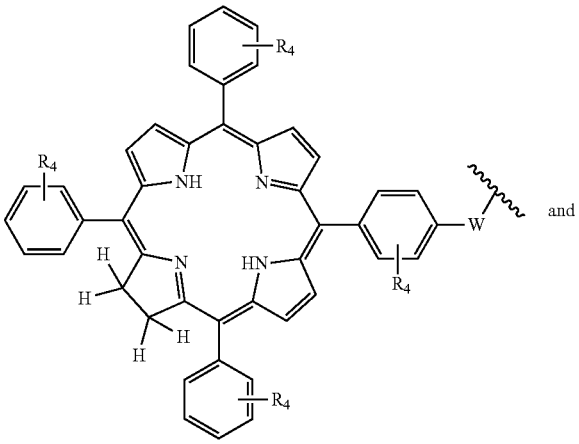 and

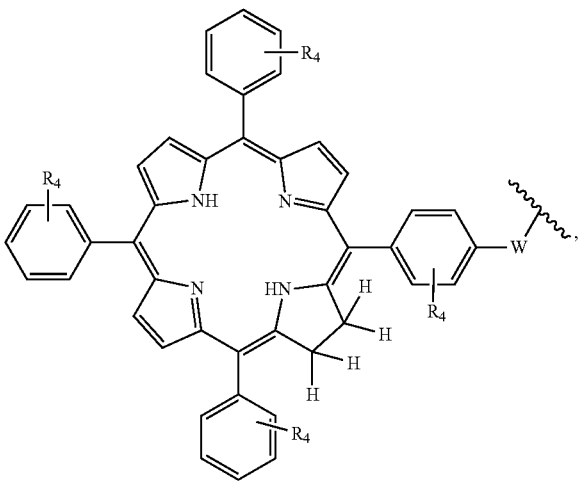,

W is a group selected from O, S, NH or $N(CH_3)$; preferably NH, $R_3$ is a group selected from:

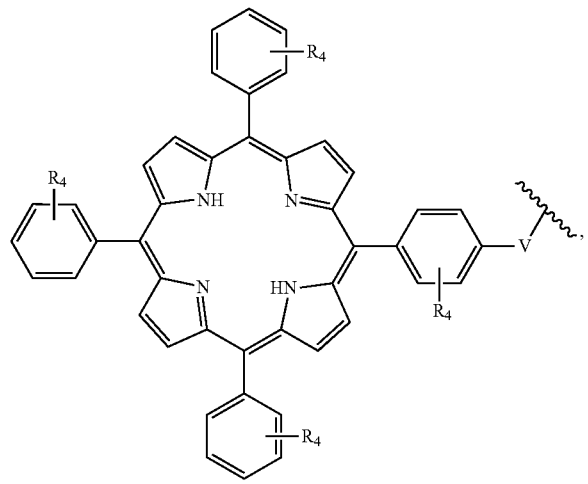

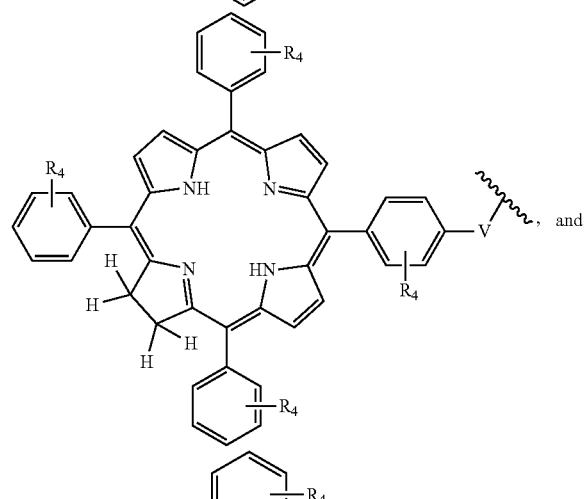

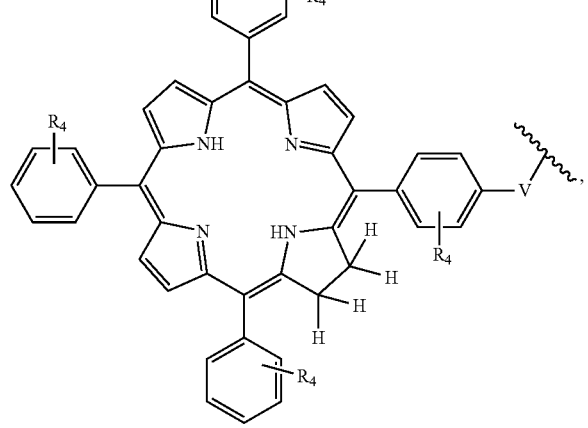

V is a group selected from CO, SO$_2$, PO, PO$_2$H or CH$_2$; preferably CO, and $R_4$ is a group (substituted in the o, m or p position), which may be the same or different, selected from H, —OH, —OCH$_3$, —CH$_3$, —COCH$_3$, C(CH$_3$)$_4$, —NH$_2$, —NHCH$_3$, —N(CH$_3$)$_2$ and —NCOCH$_3$, preferably H, wherein each R group may be the same or different.

The chitosan polymer has at least 3 units (n=3). However, preferably n is at least 10, 20, 50, 100, 500, 1000 e.g. from 10 to 100 or 10 to 50.

In a preferred embodiment $R_2$ is selected from

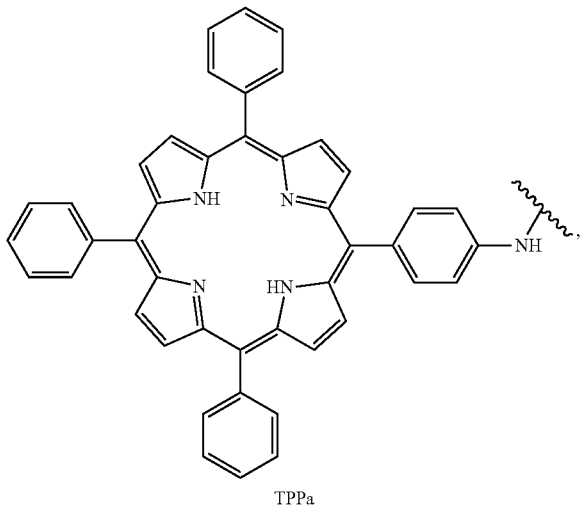

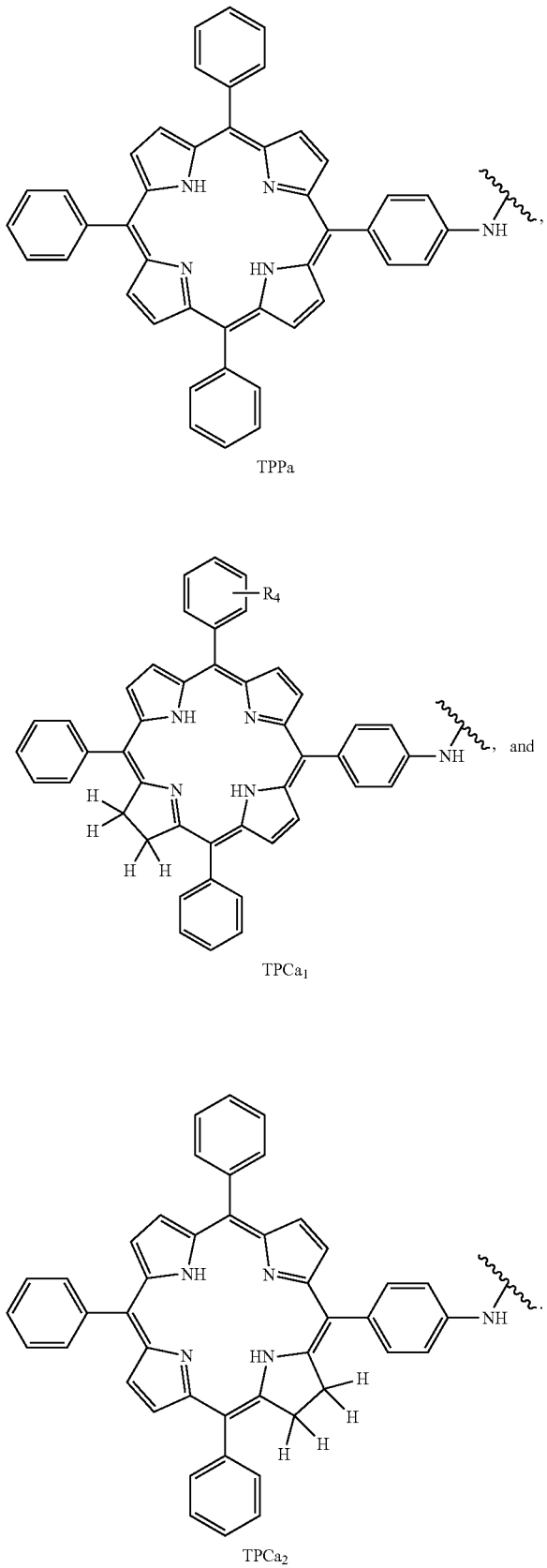

In a further preferred embodiment R₃ is selected from
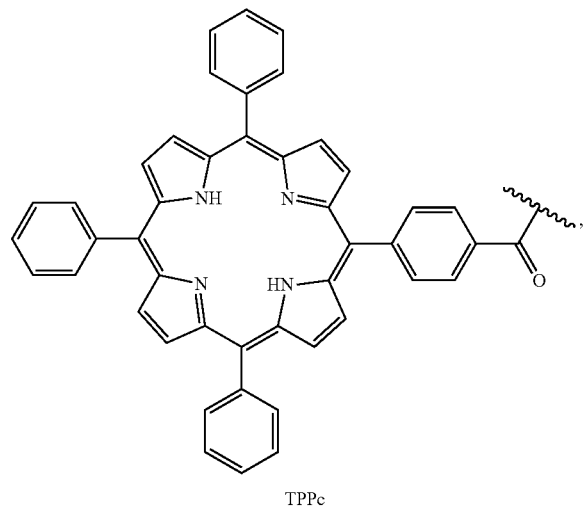
TPPc
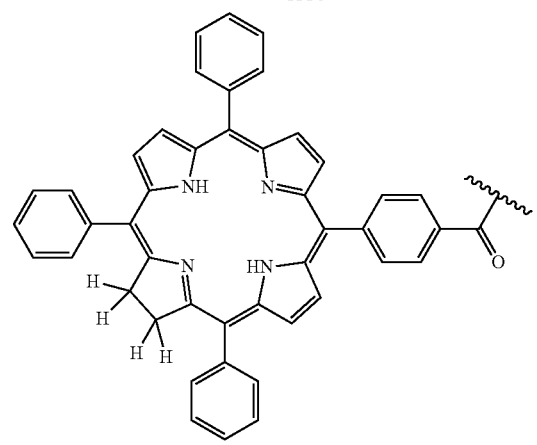
TPCc₁
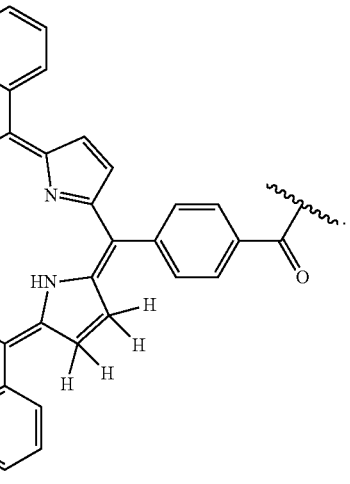
TPCc₂
Preferably $R_2$ or $R_3$ is $TPP_a$, $TPC_{a1}$ or $TPC_{c1}$.
Group A may provide 70 to 95% of the total Rn groups and group B may provide 5 to 30% of the total Rn groups.
In a most preferred embodiment the conjugate of a photosensitiser and chitosan is selected from:
17
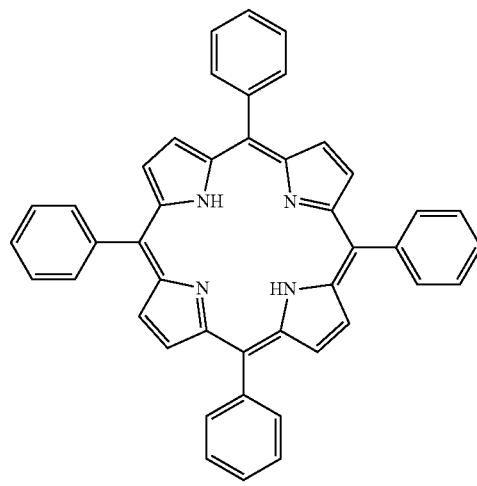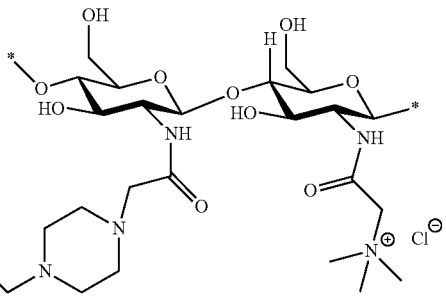
B: 25%, A: 75%

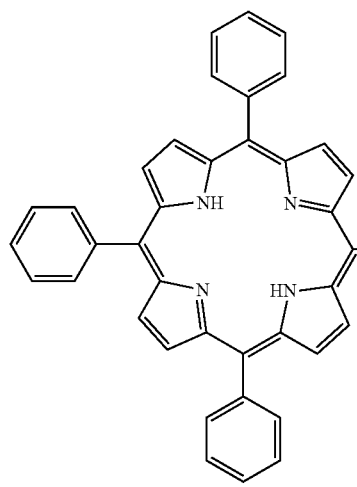
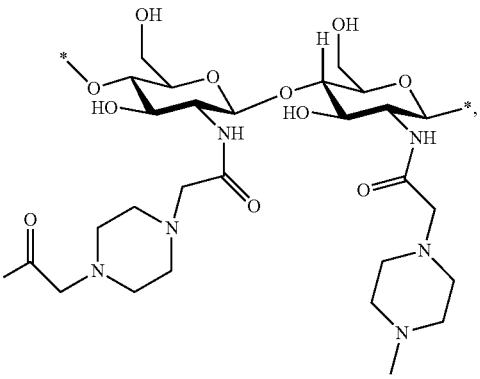
19
B: 25%, A: 75%
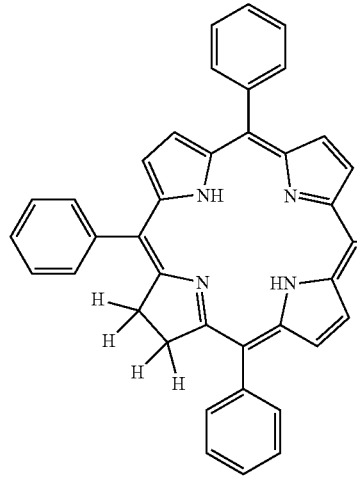
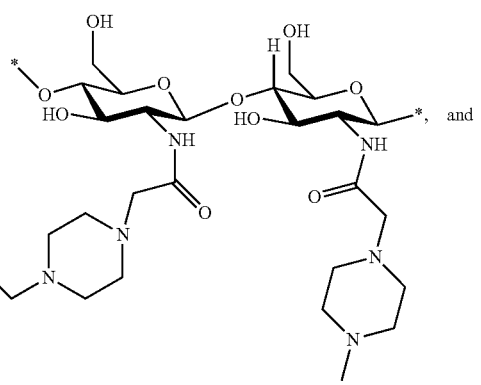
33
, and
B: 10%, A: 90%

37

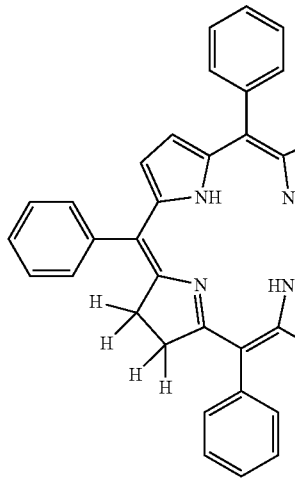
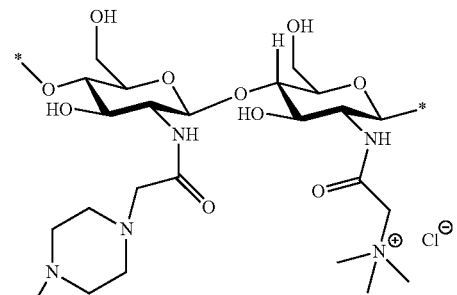

B: 10%, A: 90%

In the above structures, the A/B % values provided refer to the proportion of Rn groups which are group A or B. The asterisks denote the remainder of the chitosan polymer.

These compounds may be made by synthesis methods which utilise procedures standard in the art, which will be familiar to the skilled man and which are described in detail in WO2013/189663 which is incorporated herein by reference.

An "antigenic" molecule as referred to herein is a molecule which itself, or a part thereof, is capable of stimulating an immune response, when presented to the immune system or immune cells in an appropriate manner. Advantageously, therefore the antigenic molecule will be a vaccine antigen or vaccine component, such as a polypeptide containing entity. As discussed below the antigenic molecule may comprise more than one antigen, e.g. two or more antigenic peptides.

Many such antigens or antigenic vaccine components are known in the art and include all manner of bacterial or viral antigens or indeed antigens or antigenic components of any pathogenic species including protozoa or higher organisms. Whilst traditionally the antigenic components of vaccines have comprised whole organisms (whether live, dead or attenuated) i.e. whole cell vaccines, in addition sub-unit vaccines, i.e. vaccines based on particular antigenic components of organisms e.g. proteins or peptides, or even carbohydrates, have been widely investigated and reported in the literature. Any such "sub-unit"-based vaccine component may be used as the antigenic molecule of the present invention.

However, the invention finds particular utility in the field of peptide vaccines. Thus, a preferred antigenic molecule according to the invention is a peptide (which is defined herein to include peptides of both shorter and longer lengths i.e. peptides, oligopeptides or polypeptides, and also protein molecules or fragments thereof e.g. peptides of 5-500 e.g. 10 to 250 such as 15 to 75, or 8 to 25 amino acids).

A vast number of peptide vaccine candidates have been proposed in the literature, for example in the treatment of viral diseases and infections such as AIDS/HIV infection or influenza, canine parvovirus, bovine leukaemia virus, hepatitis, etc. (see e.g. Phanuphak et al., Asian Pac. J. Allergy.

Immunol. 1997, 15(1), 41-8; Naruse, Hokkaido Igaku Zasshi 1994, 69(4), 811-20; Casal et al., J. Virol., 1995, 69(11), 7274-7; Belyakov et al., Proc. Natl. Acad. Sci. USA, 1998, 95(4), 1709-14; Naruse et al., Proc. Natl. Sci. USA, 1994 91(20), 9588-92; Kabeya et al., Vaccine 1996, 14(12), 1118-22; Itoh et al., Proc. Natl. Acad. Sci. USA, 1986, 83(23) 9174-8. Similarly bacterial peptides may be used, as indeed may peptide antigens derived from other organisms or species.

In addition to antigens derived from pathogenic organisms, peptides have also been proposed for use as vaccines against cancer or other diseases such as multiple sclerosis. For example, mutant oncogene peptides hold great promise as cancer vaccines acting as antigens in the stimulation of cytotoxic T-lymphocytes. (Schirrmacher, Journal of Cancer Research and Clinical Oncology 1995, 121, 443-451; Curtis Cancer Chemotherapy and Biological Response Modifiers, 1997, 17, 316-327). A synthetic peptide vaccine has also been evaluated for the treatment of metastatic melanoma (Rosenberg et al., Nat. Med. 1998, 4(3), 321-7). A T-cell receptor peptide vaccine for the treatment of multiple sclerosis is described in Wilson et al., J. Neuroimmunol. 1997, 76(1-2), 15-28. Any such peptide vaccine component may be used as the antigenic molecule of the invention, as indeed may any of the peptides described or proposed as peptide vaccines in the literature. The peptide may thus be synthetic or isolated or otherwise derived from an organism.

In a preferred embodiment of the present invention the antigen is a melanoma antigen. The "melanoma antigen" can include one or more different antigens.

For example, in one aspect, the melanoma antigen is a melanoma protein or peptide, for example an antigenic peptide or T-cell epitope, for example one or more selected from gp100, Melan-A, tyrosinase, MAGE-1, MAGE-3 and tyrosinase related protein-2 (TRP-2) or a peptide epitope thereof. Details of these and further suitable melanoma antigens are disclosed in Renkvist et at, Cancer Immunol. Immunother. 50:3-15, 2001 (and references therein), and Hodi, Clin. Cancer. Res. 12:673-678, 2006, which are hereby incorporated by reference. In particular, gp100, Melan-2, tyrosinase, MAGE-1, MAGE-3 and TRP-2 and their peptide epitopes are as described in Renkvist et al., supra. Thus the invention extends to use of gp100, Melan-2, tyrosinase, MAGE-1, MAGE-3 or TRP-2, or an antigen comprising or consisting of their disclosed peptide epitopes, as disclosed in Renkvist et al., supra or a sequence with at least 95% sequence identity thereto (over a relevant window of comparison) using standard comparison techniques known in the art, or any combination thereof. In a preferred embodiment the antigen is TRP-2 and/or gp100, preferably TRP-2.

Peptide antigens, for example up to at least 200 amino acids, may be obtained from companies performing custom peptide synthesis, e.g. United BioSystems Inc (formerly United Peptide Corp., Herndon, Va., USA).

In an alternative preferred embodiment the antigenic molecule is derived from a Human Papilloma Virus (HPV). The papillomavirus genome is divided into an early region (E), encoding six (E1, E2, E4, E5, E6, and E7) open reading frames (ORF) that are expressed immediately after initial infection of a host cell, and a late region (L) encoding a major capsid protein L1 and a minor capsid protein L2. All viral ORFs are encoded on one DNA strand.

In a preferred embodiment the antigenic molecule comprises a protein or peptide, or fragment thereof, i.e. an antigen from a Human papillomavirus (HPV) (e.g. is derived from said virus) which is preferably a protein or part thereof of one of the early or late proteins referred to herein. Thus, the HPV antigen can be one or more known antigenic peptide or T-cell epitope, for example one or more selected from any known antigen from any type of HPV. Details of HPV types and antigens can be found in Ma et al. Current Cancer Therapy Reviews 6: 81-103, 2010.

For example, the antigenic peptide may be derived from HPV-16 and/or HPV-18 type HPV, or type 31 or type 45 HPV. For example, the antigen may be derived from any of the E1, E2, E4, E5, E6 or E7 proteins or any of the L1 and L2 proteins. The antigenic peptide may be derived from one or more of the E2, E6, and E7 proteins of HPV-16 and 18. In a preferred embodiment the antigenic molecule contains the HPV-16 E7 sequence GQAEPDRAHYNIVTFCCKCD-STLRLCVQSTHVDIR (the CD8 epitope is shown in bold). Thus, the HPV antigen may be a 35 amino acid peptide. Alternatively, the antigenic molecule may be only the CD8 epitope RAHYNIVTF, i.e. a shorter peptide.

HPV peptide antigens may be obtained from companies performing custom peptide synthesis, e.g. United BioSystems Inc (formerly United Peptide Corp., Herndon, Va., USA).

As discussed above the antigenic molecule according to the invention may comprise one or more antigens (as separate molecules), e.g. two or more antigens. For example, when the antigenic molecule is an antigenic peptide it may comprise one or more antigenic peptides. Thus a mix of antigens may be used as the antigenic molecule. This may be, for example, a mix of different peptides which may represent, for example different regions (and epitopes) of the same protein antigen or may represent selected regions (epitopes) from different protein antigens (e.g. that are expressed in the same tumour type). If separate antigens are used they may be used separately, simultaneously or sequentially in uses or methods of the invention. For example 2, 3 or 4 antigens may be used in the methods or uses described herein. Similarly, antigenic molecules which form an aspect in other embodiments of the invention described herein, e.g. in compositions, uses, products and kits described herein, may similarly comprise more than one antigen. In the alternative the antigenic molecule may be a single molecule containing one or more epitopes.

Once released in the cell cytosol by the photochemical internalisation process, the antigenic molecule may be processed by the antigen-processing machinery of the cell. Thus, the antigenic molecule expressed or presented on the surface of the cell may be a part or fragment of the antigenic molecule which is internalised (endocytosed). A "part" of an antigenic molecule which is presented or expressed preferably comprises a part which is generated by antigen-processing machinery within the cell. Parts may, however, be generated by other means which may be achieved through appropriate antigen design (e.g. pH sensitive bonds) or through other cell processing means. Conveniently such parts are of sufficient size to generate an immune response, e.g. in the case of peptides greater than 5, e.g. greater than 10 or 20 amino acids in size.

A "checkpoint inhibitor" as defined herein is an agent that targets an immune checkpoint, i.e. is a checkpoint inhibitor. Immune checkpoints include checkpoint proteins and lipids, for example. Checkpoint proteins regulate the immune system by identifying which cells are healthy and which cells should be destroyed by the immune system. If a cell does not have sufficient (or sufficiently activated) checkpoint proteins on its surface or on the surface of relevant T cells, it may be destroyed by the immune system, and thus checkpoint proteins act as a "brake" on the immune system.

One of the best known checkpoint proteins is cytotoxic T-lymphocyte antigen-4, or CTLA4 (also known as CD152 (cluster of differentiation 152)). This molecule is a protein receptor that downregulates the immune response. CTLA4 is found on the surface of T cells, which lead the cellular immune attack on antigens. The T cell attack can be turned off by stimulating the CTLA4 receptor, which acts as an "off" switch. Once a cytotoxic T cell becomes active it expresses CTLA4 on its surface, which then competes with the co-stimulatory molecule CD28 for their mutually shared ligands, B7-1 and B7-2 on antigen-presenting cells. This balance holds cytotoxic activity in check, while allowing T cell function to proceed in a self-limited manner.

A further example of a checkpoint protein is PD-L1 (Programmed Death Ligand 1), which is a 40 kDa type 1 transmembrane protein. The receptor for PD-L1 is PD-1, which is a cell surface receptor that belongs to the immunoglobulin superfamily and is expressed on T cells and pro-B cells. The formation of PD-1 receptor/PD-L1 ligand complex transmits an inhibitory signal which reduces the proliferation of CD8+ T cells at lymph nodes, and supplementary to that PD-1 is also able to control the accumulation of foreign antigen-specific T cells in the lymph nodes through apoptosis. Thus, PD-L1 prevents T-cells from attacking healthy cells. When PD-L1 activates the PD-1 receptor on the surface of a T-cell, the T-cell is signalled to destroy itself.

Other checkpoint proteins include CD-137 (4-1BB) a costimulatory checkpoint protein; lymphocyte activation gene 3 (LAG-3, CD223), a CD4-related inhibitory receptor coexpressed with PD-1 on tolerant T cells; B7 superfamily proteins B7-H3 and B7-H4 and T cell protein TIM3. Phospholipids may also act as a checkpoint molecule, e.g. phosphatidylserine (PS) which is a phospholipid in normal cells that is translocated to the outer member surface during apoptosis, suppressing the excess immune activation that would otherwise occur during processing and clearance of decaying cell matter. Externalization of PS indirectly stimulates macrophages, resulting in suppression of dendritic cell antigen presentation. Like PD-L1, externalized PS is aberrantly expressed by some tumour cells and tumour-derived microvesicles.

The checkpoint inhibitor according to the present invention may target or inhibit the activity of any of these checkpoint molecules (such as checkpoint proteins or lipids) by interaction with the checkpoint molecules themselves or with their binding partners, e.g. ligands.

Checkpoint inhibitors (also known as immune checkpoint modulators, or CPMs) lessen the effect of checkpoint molecules on preventing cell death achieved through T/B cell activation. The ability to inhibit a checkpoint molecule may be assessed in an appropriate model, e.g. by preventing binding to its binding partner, e.g. to B7-1 or B7-2 (for CTLA-4) or to PD-L1 (for PD-1).

Several checkpoint inhibitors are known and can be used in the present invention, for example those inhibitors described in Creelan (2014) Cancer Control 21:80-89, which is hereby incorporated by reference.

The checkpoint inhibitor may be an antibody, and suitable antibodies are commercially available. Preferably the antibody is a monoclonal antibody.

By way of example, anti-CTLA-4 and anti-PD-1 antibodies are available from Bio X Cell (West Lebanon, USA). Examples of other specific antibodies which are checkpoint inhibitors include: Tremelimumab (CP-675,206), a human IgG2 monoclonal antibody with high affinity to CTLA-4; Ipilimumab (MDX-010), a human IgG1 monoclonal antibody to CTLA-4; Nivolumab (BMS-936558), a human monoclonal anti-PD1 IgG4 antibody that essentially lacks detectable antibody-dependent cellular cytotoxicity (ADCC); MK-3475 (formerly lambrolizumab), a humanized IgG4 anti-PD-1 antibody that contains a mutation at C228P designed to prevent Fc-mediated ADCC; Urelumab (BMS-663513), a fully human IgG4 monoclonal anti-CD137 antibody; anti-LAG-3 monoclonal antibody (BMS-986016); and Bavituximab (chimeric 3G4), a chimeric IgG3 antibody against PS. Any suitable checkpoint inhibitor as discussed herein or otherwise available can be used in the present invention.

In a preferred embodiment the checkpoint inhibitor targets CTLA-4 and/or PD-1. In a preferred embodiment both a checkpoint inhibitor that targets CTLA-4 and a checkpoint inhibitor that targets PD-1 may be used (e.g. antibodies to those targets). Preferably the checkpoint inhibitor is an antibody against CTLA-4 and/or PD-1 and prevents or inhibits binding of CTLA-4 to B7-1/B7-2 and/or of PD-1 to PD-L1. As discussed herein CTLA-4 and PD-1 preferably have the sequences as set forth in UniProt Database Accession no. P1640, version 3 of the sequence (10 Jan. 2003) and Accession no. Q15116 version 3 of the sequence (17 Apr. 2007), respectively, or a sequence with at least 70, 80, 90, 95, 96, 97, 98 or 99% sequence identity thereto as assessed over the full length sequence using methods routine in the art.

An alternative strategy is to inhibit PD-L1, the ligand for PD-1, on the tumour cell surface, and therefore inhibitors of PD-L1 are also encompassed by the present invention as checkpoint inhibitors. For example, MPDL3280A (RG7446), is a human IgG1-kappa anti-PD-L1 monoclonal antibody and may be used according to the invention. MEDI4736 is another IgG1-kappa PD-L1 inhibitor.

Another alternative approach is to competitively block the PD-1 receptor, using a B7-DC-Fc fusion protein, and such fusion proteins can also therefore be used in the present invention. In a further alternative approach an antibody to Killer cell immunoglobulin-like receptor may be used as the immunotherapeutic agent. Killer cell immunoglobulin-like receptor (KIR) is a receptor on NK cells that downregulates NK cytotoxic activity. HLA class I allele-specific KIR receptors are expressed in cytolytic (CD56dimCD16+) NK cells, while CD56brightCD16-NK subset lacks these KIRs. Along these lines, inhibitory KIRs seem to be selectively expressed in the peritumoral NK cell infiltrate and thus seem to be a checkpoint pathway co-opted by tumours, similar to PD-L1. As such, inhibition of specific KIRs using antibodies should cause sustained in vivo activation of NK cells. For example, lirilumab (IPH2102) is fully human monoclonal antibody to KIR and can be used according to the invention.

In methods of the invention one or more (e.g. two or more) checkpoint inhibitors may be used, which may be used separately, simultaneously or sequentially. For example 2, 3 or 4 checkpoint inhibitors may be used in the method, e.g. checkpoint inhibitors to CTLA4 and PD-1, e.g. anti-CTLA4 and anti-PD-1. Similarly, one or more checkpoint inhibitors may be provided in other embodiments of the invention described herein, e.g. in compositions, uses, products and kits described herein. Thus, in embodiments of the invention described herein reference to a checkpoint inhibitor encompasses one or more checkpoint inhibitors.

In a preferred embodiment, the methods of the present invention additionally involve the use of a ligand for a Toll-like receptor (TLR). In all aspects of the invention one or more (e.g. two or more) TLR ligands may be used, which may be used separately, simultaneously or sequentially. Thus, in embodiments of the invention described herein reference to a TLR ligand encompasses one or more TLR ligands.

Toll-like receptors are a class of proteins that play a key role in the innate immune system as well as the digestive system. TLRs and Interleukin-1 receptors form a receptor superfamily, named the Interleukin-1 Receptor/Toll-like Receptor superfamily. All members of this family have a Toll-IL-1 receptor domain (TIR). Members of the interleukin-1 receptor (IL-1R) family are characterized by extracellular immunoglobulin-like domains and intracellular Toll/Interleukin-1R (TIR) domain. Receptors with subgroup 2 TIR domains are considered TLRs.

TLRs are single, membrane-spanning, non-catalytic receptors usually expressed in sentinel cells such as macrophages and dendritic cells, that recognize structurally conserved molecules derived from microbes. Once these microbes have breached physical barriers such as the skin or intestinal tract mucosa, they are recognized by TLRs, which activate immune cell responses. These receptors recognize molecules such as pathogen-associated molecules, which are thought to be critical to the pathogen's function and difficult to change through mutation. They may include bacterial cell-surface lipopolysaccharides (LPS), lipoproteins, lipopeptides, and lipoarabinomannan; proteins such as flagellin from bacterial flagella; double-stranded RNA of viruses; or the unmethylated CpG islands of bacterial and viral DNA; and also of the CpG islands found in the promoters of eukaryotic DNA; as well as certain other RNA and DNA molecules. For most of the TLRs, ligand recognition specificity has now been established by gene targeting.

It has been estimated that most mammalian species have between ten and fifteen types of Toll-like receptor. Thirteen TLRs (named simply TLR1 to TLR13) have been identified in humans and mice together (thirteen in mouse and ten in humans).

All ligands for TLR receptors are encompassed by the present invention. The term "ligand" is intended to mean a substance that forms a complex with a biomolecule to serve a biological purpose. In the context of a TLR ligand, it is a signal triggering molecule, binding to a site on a target TLR. When a ligand binds to its cognate receptor it may alter the chemical conformation of the receptor. The conformational state of a receptor protein determines its functional state.

Thus, a TLR ligand according to the present invention is a molecule that binds to at least one, or one or more, toll-like receptor (TLR) and results in activation of the TLR, for example activation of TLR-mediated cell signalling.

TLR signaling is divided into two distinct signaling pathways, the MyD88-dependent and TRIF-dependent pathway. A TLR ligand according to the invention activates one or both of these two pathways. Thus, a ligand according to the present invention is a molecule that binds to one or more TLRs and results in activation of the TLR, for example activation of TLR signalling via a conformational change of the receptor on binding of the ligand.

The MyD88-dependent response occurs on dimerization of the TLR receptor, and is utilized by every TLR except TLR3. Its primary effect is activation of NFκB and Mitogen-activated protein kinase. Ligand binding and conformational change that occurs in the receptor recruits the adaptor protein MyD88, a member of the TIR family. MyD88 then recruits IRAK 4, IRAKI and IRAK2. IRAK kinases then phosphorylate and activate the protein TRAF6, which in turn polyubiquinates the protein TAK1, as well as itself in order to facilitate binding to IKKβ. On binding, TAK1 phosphorylates IKKβ, which then phosphorylates IκB causing its degradation and allowing NFκB to diffuse into the cell nucleus and activate transcription and consequent induction of inflammatory cytokines.

The other pathway is the TRIF-dependent pathway, which is used by both TLR3 and TLR4. For TLR3, dsRNA (or similar—see below) leads to activation of the receptor, recruiting the adaptor TRIF. TRIF activates the kinases TBK1 and RIP1, which creates a branch in the signaling pathway. The TRIF/TBK1 signaling complex phosphorylates IRF3 allowing its translocation into the nucleus and production of Interferon type I. Meanwhile, activation of RIP1 causes the polyubiquination and activation of TAK1 and NFκB transcription in the same manner as the MyD88-dependent pathway.

Standard methods for determining activation of TLR signalling are known in the art, for example determination of the phosphorylation state of appropriate signalling proteins. Alternatively, one may determine whether a ligand acts through a TLR by well known methods in the art, e.g. by genetically deleting the gene encoding the specific TLR and determining whether the effect of the ligand is maintained. This method can be used both in vitro and in vivo in transgenic knock-out mice, which are commercially available (TLR2, 3 and 4 knock-outs are available from The Jackson Laboratory and TLR 1, 2, 3, 4, 5, 6, 7 and 9 knock-outs from OrientalBioService Inc). In addition, HEK-Blue™ cells (Invivogen, San Diego, Calif., USA) are available which are designed to study stimulation of TLRs via assaying NF-κB/AP1 activation. Such cells are available for TLRs 2-9 and 13. Also, TLR antagonists such as those available from Invivogen can be used to determine whether antagonism of the TLR inhibits the action of a putative ligand. Thus, methods of determining whether a molecule is a TLR ligand, e.g. a specific TLR ligand, are well known in the art.

The structure of a TLR consists of a leucine-rich repeat (LRR) ectodomain, a helical transmembrane domain, and an intracellular Toll/IL-1 receptor homology (TIR) signaling domain. The ectodomain contains varying numbers of LRRs and resembles a solenoid bent into a horseshoe shape. At both ends there is a terminal LRR that shields the hydrophobic core of the horseshoe. These ectodomains are highly variable. They are directly involved in the recognition of a variety of pathogen-associated motifs including lipopolysaccharide, lipopeptide, cytosine-phosphate-guanine (CpG) DNA, flagellin, imidazoquinoline, and ds/ssRNA. Upon receptor activation, a TIR signaling complex is formed between the receptor and adaptor TIR domains.

The receptors TLR 7, 8, and 9 are a family with a longer amino acid sequence than other TLRs. They are localized intracellularly and signal in response to non-self nucleic acids. They also contain an irregular segment between their LRR14 and 15.

The sequences of TLR receptors are known and binding to those receptors by ligands described herein may be assessed, e.g. as described hereinbefore. By way of example, known TLR amino acid sequences are shown in Table 1 below.

TABLE 1

| TLR | NCBI Reference Sequence | UniProtKB/ Swiss-Prot Reference |
| --- | --- | --- |
| toll-like receptor 1 precursor (Homo sapiens) | NP_003254.2 | Q15399 |
| toll-like receptor 2 precursor (Homo sapiens) | NP_003255.2 | O60603 |
| toll-like receptor 3 precursor (Homo sapiens) | NP_003256.1 | O15455 |
| toll-like receptor 4 isoform C (Homo sapiens) | NP_003257.1 | O00206 |
| toll-like receptor 5 precursor (Homo sapiens) | NP_003259.2 | O60602 |
| toll-like receptor 6 precursor (Homo sapiens) | NP_006059.2 | Q9Y2C9 |
| toll-like receptor 7 precursor (Homo sapiens) | NP_057646.1 | Q9NYK1 |
| toll-like receptor 8 precursor (Homo sapiens) | NP_619542.1 | Q9NR97 |
| toll-like receptor 9 precursor (Homo sapiens) | NP_059138.1 | Q9NR96 |
| toll-like receptor 10 isoform a (Homo sapiens) | NP_001017388.1 | Q9BXR5 |
| toll-like receptor 11 (mouse) | | Q6R5P0 |
| toll-like receptor 12 (mouse) | | Q6QNU9 |
| toll-like receptor (mouse) | | Q6R5N8 |

TLR1 is a cell-surface receptor whose ligands include lipoproteins and multiple triacyl lipopeptides, such as those derived from bacteria. TLR 1 does not recognize ligands on its own, rather it acts in a complex with TLR 2. Thus, ligands recognise a complex between TLR1 and TLR2. TLR1 recognises peptidoglycan and (triacyl) lipoproteins in combination with TLR2 (as a heterodimer).

A lipoprotein/peptide is a molecule consisting of a lipid connected to a protein/peptide. Bacteria express such molecules. A triacyl lipoprotein/peptide comprises three acyl groups. Preferably the TLR1 ligand for use according to the invention is a triacyl lipopeptide.

TLR1 ligands can be purchased from Invivogen or Enzo Life Sciences (Farmingdale, N.Y., USA). For example, Pam3CSK4 (Invivogen) is a synthetic triacylated lipopeptide (LP) that mimics the acylated amino terminus of bacterial LPs.

Alternatively, Pam3Cys-Ser-(Lys)4 trihydrochloride (Enzo Life Sciences) may be used which is a selective agonist of TLR1 complexed with TLR2.

TLR2 is a cell surface receptor which is stimulated by a wide array of microbial molecules representing broad groups of species both of Gram-positive and Gram-negative bacteria, as well as *mycoplasma* and yeast. TLR2 recognizes cell-wall components such as peptidoglycan, lipoteichoic acid and lipoprotein from gram-positive bacteria, lipoarabinomannan from mycobacteria, and zymosan from yeast cell wall.

Preferred TLR2 ligands are lipoglycans, such as lipoarabinomannan and lipomannan from *Mycobacterium smegmatis*. Particularly preferred lipoglycans are lipopolysaccharides (LPS) specific for TLR2. These molecules have a lipid and polysaccharide joined by a covalent bond and are found in the outer member of Gram-negative bacteria and act as endotoxins. In a preferred feature the LPS is from *Porphyromonas Gingivalis*. LPS consists of a polysaccharide region that is anchored in the outer bacterial membrane by a specific carbohydrate lipid moiety termed lipid A. Lipid A, also known as endotoxin, is responsible for the immunostimulatory activity of LPS.

The most active form of lipid A contains six fatty acyl groups and is found in pathogenic bacteria such as *Escherichia coli* and *Salmonella* species.

Other preferred TLR2 ligands are lipoteichoic acids e.g. which originate from different bacterial species such as *Bacillus subtilis* and *Staphylococcus aureus*; peptidoglycans, e.g. from bacterial species such as *Bacillus subtilis, E. coli* strains (e.g. 0111:B4 or K12), *Staphylococcus aureus*, and others; synthetic lipoproteins such as synthetic diacylated lipoprotein or synthetic triacylated lipoprotein and zymosan (e.g. from *Saccharomyces cerevisiae*) which is a glucan with repeating glucose units connected by β-1,3-glycosidic linkages. TLR2 ligands are commercially available from Invivogen.

TLR3 is found in cellular compartments. Preferred ligands according to the invention are double-stranded RNA molecules mimicking viral dsRNA, e.g. Polyadenylic-polyuridylic acid (Poly(A:U)) or Polyinosine-polycytidylic acid (Poly(I:C)). Poly(I:C) is particularly preferred.

Double-stranded RNA (dsRNA) is RNA with two complementary strands, similar to the DNA found in all cells. dsRNA forms the genetic material of some viruses (double-stranded RNA viruses). Double-stranded RNA such as viral RNA or siRNA can trigger RNA interference in eukaryotes, as well as an interferon response in vertebrates.

In a preferred feature the ligand is Poly(I:C). Poly I:C is a mismatched double stranded RNA with one strand being a polymer of inosinic acid, the other a polymer of cytidylic acid. Such molecules may be generated by well known techniques. Various commercial sources exist, e.g. the following may be purchased from Invivogen and form preferred embodiments:

Poly(I:C) (HMVV) with a high molecular weight and an average size of 1.5-8 kb, and
Poly(I:C) (LMW) with a low molecular weight and an average size of 0.2-1 kb. Both high and low molecular weight forms are preferred forms for use according to the present invention.

TLR4 is also found on the cell surface and has several ligand types, including inter alia lipopolysaccharides (LPS), several heat shock proteins, fibrinogen, heparin sulphate fragments, hyaluronic acid fragments, nickel and various opioid drugs. In a preferred aspect the ligand is LPS. The LPS may originate from various bacterial species, e.g. from *E. coli* 0111:B4 or K12 or *Salmonella* (extracted by a phenol-water mixture), in a preferred feature the LPS is from *E. coli* or from *Salmonella minnesota* e.g. strain R595.

In another preferred aspect the TLR4 ligand is Monophosphoryl Lipid A (MPLA) which may be isolated from bacteria (e.g. *Salmonella minnesota* R595), or made synthetically. In general, TLR4 ligands are available commercially e.g. from Invivogen.

TLR5 binds to the ligand flagellin from both Gram-positive and Gram-negative bacteria such as *Bacillus subtilis, Pseudomonas aeruginosa, Salmonella typhimurium* and others. Flagellin is a globular protein that arranges itself in a hollow cylinder to form the filament in bacterial flagellum. It has a mass of about 30,000 to 60,000 daltons. Flagellin is the principal substituent of bacterial flagellum, and is present in large amounts on nearly all flagellated bacteria. Thus, preferred TLR5 ligands are flagellins, preferably from a bacteria as described above. TLR5 ligands are available commercially e.g. from Invivogen.

TLR6 binds to multiple diacyl lipopeptides. As discussed above, lipopeptides are found in bacteria and comprise a lipid joined to a peptide. A diacyl lipopeptide has 2 acyl groups and forms a preferred TLR6 ligand for use according to the invention. TLR6 ligands are available commercially from Invivogen. For example, FSL-1 (Pam2CGDPKHPKSF) is a synthetic lipoprotein derived from *Mycoplasma salivarium* similar to MALP-2, a *M. fermentans* derived lipopeptide (LP). Mycoplasmal LPs, such as FSL-1, contain a diacylated cysteine residue, whereas bacterial LP contain a triacylated one. FSL-1 is recognized by TLR6 in combination with TLR2, whereas bacterial LPs are recognized by a combination of TLR2 and TLR1 as discussed above.

TLR7 ligands include the small synthetic compounds imidazoquinoline, base analogs such as adenine and guanosine analogs (e.g. loxoribine) and bropirimine, and also single-stranded RNA.

Imidazoquinoline compounds are double cyclic organic molecules, preferably with the formula indicated below in which the groups at $R_1$ and $R_2$ may be varied.

Preferably the imidazoquinoline compound has the formula 1:

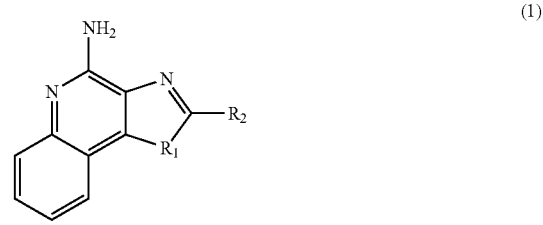

(1)

wherein $R_1$ is an amino-alkyl group, optionally substituted, e.g. with a hydroxyl group and $R_2$ is an alkyl group optionally interrupted with an oxygen or nitrogen group; wherein preferably
$R_1$, is N—CH$_2$—C(CH$_3$)$_2$—R$_3$;
$R_2$ is —CH$_2$—X—CH$_2$CH$_3$ or a hydrogen atom;
$R_3$ is OH or a hydrogen atom and X is O or NH;
or a pharmaceutically acceptable salt thereof.

In the above formula an alkyl group may be a $C_1$-$C_{10}$ group.

Examples of these compounds are known in the art, e.g. Resiquimod (or R848) (1-[4-amino-2-(ethoxymethyl)imidazo[4,5-c]quinolin-1-yl]-2-methylpropan-2-ol), Imiquimod (3-(2-methylpropyl)-3,5,8-triazatricyclo[7.4.9.0$^{2,6}$]trideca-1(9),2(6),4,7,10,12-hexaen-7-amine) and gardiquimod (R1 is N—CH$_2$—C(CH$_3$)$_2$OH; R$_2$ is —CH$_2$—NH—CH$_2$CH$_3$; 1-[4-Amino-2-(ethylaminomethyl)imidazo[4,5-c]quinolin-1-yl]-2-methylpropan-2-ol) (all available from InvivoGen (San Diego Calif., USA)). In a preferred embodiment the compound is selected from Resiquimod and Imiquimod.

Pharmaceutically acceptable salts of these compounds are also encompassed in the invention. Appropriate salts include for example acetate, bromide, chloride, citrate, hydrochloride, maleate, mesylate, nitrate, phosphate, sulphate, tartrate, oleate, stearate, tosylate, calcium, meglumine, potassium and sodium salts.

Loxoribine is a guanosine analog derivatized at position $N^7$ and $C^8$. This nucleoside is a very powerful stimulator of the immune system.

Bropirimine is an experimental drug with anti-cancer and antiviral properties with the structure as shown below:

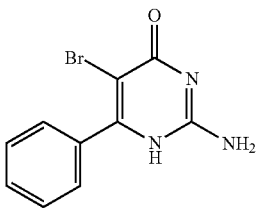 [SMILES: Nc1nc(=O)c(Br)c(-c2ccccc2)[nH]1]

Single stranded RNA is a preferred TLR7 ligand, e.g. ssPolyU, wherein preferably said single stranded molecule is between 20 and 200 nucleotides in length. Such molecules can be readily generated synthetically.

TLR8 ligands are generally small synthetic compounds or single-stranded RNA. Preferably said TLR8 ligand is an ssPolyU molecule as described above.

TLR9 ligands include unmethylated CpG Oligodeoxynucleotide DNA. A "CpG" oligonucleotide (or CpG ODN) is an example of such a ligand, and is a short single-stranded synthetic DNA molecule that results from binding a cytosine triphosphate deoxynucleotide ("C") to a guanine triphosphate deoxynucleotide ("G"). The "p" refers to the phosphodiester link between consecutive nucleotides, although some ODN have a modified phosphorothioate (PS) backbone instead. As referred to herein the CpG nucleotides are referred to as the CpG motif. The CpG motif is unmethylated. Sequences containing CpG motifs are considered pathogen-associated molecular patterns (PAMPs) due to their abundance in microbial genomes but their rarity in vertebrate genomes. The CpG PAMP is recognized by the pattern recognition receptor (PRR) Toll-Like Receptor 9 (TLR9). TLR9 recognizes specific unmethylated CpG oligonucleotides (ODN) sequences that distinguish microbial DNA from mammalian DNA.

Three main types of stimulatory ODNs have been described: type A, B and C. Type A CpG ODNs are constructed of a mixed phosphodiester/phosphorothioate backbone, and contain one or more CpG motif as part of a palindromic sequence. Type A CpG ODNs have poly G tails at the 3' and 5' ends (a structural motif that facilitates the formation of concatemers). Type A CpG ODNs typically contain 7 to 10 phosphorothioate-modified bases at one or both ends that resist degradation by nucleases and increase the stability of the ODN. For example, the internal palindrome sequence can be 8 to 16 (preferably 10, 12 or 14) base pairs in length and varies in the order of bases, however the pattern, 5'-Pu Pu CG Pu: Py CG Py Py-3', wherein the Pu, Py bases equidistant from the palindrome centre, marked with ":", are complementary, is preferred. The poly G tail found at either end of the DNA strand can vary in length.

Type B CpG ODNs may have one or more timer consensus sequences containing the CpG motif. A human consensus sequence may contain the sequence 5'-Pu Py C G Py Pu-3'. (Mouse sequences may be different.) Type B CpG ODNs have a fully phosphorothioated (PS-modified) backbone, and are generally 18 to 28 (e.g. 18-22) nucleotides in length. An example of a type B CpG ODN is ODN 1826 which has the sequence 5'-tccatgacgttcctgacgtt-3'.

Type C CpG ODNs combine features of both types A and B. Type C CpG ODNs are composed entirely of phosphorothioate nucleotides and contain palindromic sequences containing one or more CpG motif. An example of a type C CpG ODN is ODN 2395 which has the sequence 5'-tcgtcgtttt<u>cggcgc:gcgccg</u>-3'

(palindrome underlined).

In addition, Type P CpG ODNs which contain two palindromic sequences, enabling them to form higher ordered structures, may also be used.

CpG oligonucleotides can be synthesised by standard oligonucleotide synthesis methods which are known in the art.

Thus CpG oligonucleotides for use in the invention extend to a single-stranded oligonucleotide of from 6-50 bases, preferably 18-27, preferably 20-25 bases, which includes at least one CpG motif and at least one base flanking said motif on each of the 3' and 5' sides, wherein said CpG motif is a cytosine followed by a guanine linked by a phosphate or phosphorothioate bond in which the pyrimidine ring of the cytosine is unmethylated. In one embodiment, the one or more motif is flanked by sequences, which together with the one or more motif provides a palindromic sequence. As referred to herein a "palindromic sequence" provides a forward sequence linked to the complementary sequence in reverse such that the sequence may form a hairpin, e.g. cggcgc:gcgccg (in which the centre of the palindrome is marked with ":"). The CpG motif may form the centre of the sequence and/or be elsewhere in the palindromic sequence. Preferably the palindromic sequence (including both the forward and reverse sequence) is from 8 to 16, preferably 10-12 or 10-14, bases in length.

In a further preferred aspect the CpG oligonucleotide sequence contains the palindromic sequence 5'-Pu Pu CG Pu:Py CG Py Py-3', wherein the Pu, Py bases equidistant from the palindrome centre, marked with ":", are complementary, and/or one or more of the consensus sequences 5'-Pu Py CG Py Pu-3'. Optionally the CpG oligonucleotide may contain poly G tails at the 3' or 5' ends of 3 to 8 bases in length.

In a preferred embodiment of the present invention the CpG oligonucleotide is a type C CPG ODN, of 18-27 bases with a palindromic sequence of 10-14 bases and a phosphorothioate backbone. Particularly preferred is ODN 2395 which has the sequence:

5'-tcgtcgtttt<u>cggcgc:gcgccg</u>-3'

(palindromic sequence underlined).

In an alternative preferred embodiment of the present invention the CpG oligonucleotide is a type B CPG ODN, of 18-22 bases and a phosphorothioate backbone. Particularly preferred is ODN 1826 which has the sequence:

5'-tccatgacgttcctgacgtt-3'.

TLR11 and 12 ligands include profilin, which is an actin-binding protein involved in the dynamic turnover and restructuring of the actin cytoskeleton. Thus a preferred TLR11/12 ligand is profilin derived from *Toxoplasma gondii*, which is an obligate, intracellular, parasitic protozoan that causes the disease toxoplasmosis. Profilin can be purchased from e.g. Enzo Life Sciences.

TLR13 ligands include the bacterial ribosomal RNA sequence "CGGAAAGACC", and nucleic acids comprising this nucleotide sequence and this ligand forms a preferred aspect of the invention. The oligonucleotide having the sequence 5'-GGACGGAAAGACCCCGUGG-3' is a TLR13 ligand and can be purchased from e.g. Invivogen.

Thus, preferably said TLR ligand is a TLR 2, 3, 4, 7, 8 or 9 ligand, preferably a ligand as described above. In a preferred embodiment the TLR ligand is a TLR 3 ligand, preferably as described above. In an alternative preferred embodiment the TLR ligand is a TLR 4 ligand, preferably as described above. In yet an alternative preferred embodiment the TLR ligand is a TLR7-9 ligand, or a TLR7 ligand, or a TLR8 ligand or a TLR 9 ligand, preferably as described above.

As used herein "expressing" or "presenting" refers to the presence of the antigenic molecule or a part thereof on the surface of said cell such that at least a portion of that molecule is exposed and accessible to the environment surrounding that cell, preferably such that an immune response may be generated to the presented molecule or part thereof. Expression on the "surface" may be achieved in which the molecule to be expressed is in contact with the cell membrane and/or components which may be present or caused to be present in that membrane.

The term "cell" is used herein to include all eukaryotic cells (including insect cells and fungal cells). Representative "cells" thus include all types of mammalian and non-mammalian animal cells, plant cells, insect cells, fungal cells and protozoa. Preferably, however, the cells are mammalian, for example cells from cats, dogs, horses, donkeys, sheep, pigs, goats, cows, mice, rats, rabbits, guinea pigs, but most preferably from humans.

In methods of the invention a first cell is used which is capable of presentation of the antigenic molecule or part thereof on its surface. The first cell which is subjected to the methods, uses etc. of the invention may thus be any cell which is capable of expressing, or presenting on its surface a molecule which is administered or transported into its cytosol.

The first cell is conveniently an immune cell i.e. a cell involved in the immune response. However, other cells may also present antigen to the immune system and these also fall within the scope of the invention. The first cells according to the present invention are thus advantageously antigen-presenting cells as described hereinafter. The antigen-presenting cell may be involved in any aspect or "arm" of the immune response as defined herein.

The stimulation of cytotoxic cells requires antigens to be presented to the cell to be stimulated in a particular manner by the antigen-presenting cells, for example MHC Class I presentation (e.g. activation of $CD8^+$ cytotoxic T-cells requires MHC-1 antigen presentation). Antibody-producing cells may also be stimulated by presentation of antigen by the antigen-presenting cells.

Antigens may be taken up by antigen-presenting cells by endocytosis and degraded in the endocytic vesicles to peptides. These peptides may bind to MHC class II molecules in the endosomes and be transported to the cell surface where the peptide-MHC class II complex may be recognised by CD4+ T helper cells and induce an immune response. Alternatively, proteins in the cytosol may be degraded, e.g. by proteasomes and transported into endoplasmic reticulum by means of TAP (transporter associated with antigen presentation) where the peptides may bind to MHC class I molecules and be transported to the cell surface (Yewdell and Bennink, 1992, Adv. Immunol. 52: 1-123). If the peptide is of foreign antigen origin, the peptide-MHC class I complex will be recognised by CD8+ cytotoxic T-cells (CTLs). The CTLs will bind to the peptide-MHC (HLA) class I complex and thereby be activated, start to proliferate and form a clone of CTLs. The target cell and other target cells with the same peptide-MHC class I complex on the cells surface may be killed by the CTL clone. Immunity against the foreign antigen may be established if a sufficient amount of the antigen can be introduced into the cytosol (Yewdell and Bennink, 1992, supra; Rock, 1996, Immunology Today 17: 131-137). This is the basis for development of inter alia cancer vaccines. One of the largest practical problems is to introduce sufficient amounts of antigens (or parts of the antigen) into the cytosol. This may be solved according to the present invention.

As mentioned previously, once released in the cell cytosol by the photochemical internalisation process, the antigenic molecule may be processed by the antigen-processing machinery of the cell and presented on the cell surface in an appropriate manner e.g. by Class I MHC. This processing may involve degradation of the antigen, e.g. degradation of a protein or polypeptide antigen into peptides, which peptides are then complexed with molecules of the MHC for presentation. Thus, the antigenic molecule expressed or presented on the surface of the cell according to the present invention may be a part or fragment of the antigenic molecule which is internalised (endocytosed).

A variety of different cell types can present antigen on their surface, including for example, lymphocytes (both T and B cells), dendritic cells, macrophages etc. Others include for example cancer cells e.g. melanoma cells. These cells are referred to herein as "antigen-presenting cells". "Professional antigen-presenting cells" which are cells of the immune system principally involved in the presentation of antigen to effector cells of the immune system are known in the art and described in the literature and include B lymphocytes, dendritic cells and macrophages. Preferably the cell is a professional antigen-presenting cell.

For antigen presentation by an antigen-presenting cell to a cytotoxic T-cell (CTL) the antigenic molecule needs to enter the cytosol of the antigen-presenting cell (Germain, Cell, 1994, 76, 287-299).

In embodiments of the invention, for example involving an in vitro or ex vivo method, or alternatively an in vivo method, the first cell (or the cell which presents antigen in the in vivo method) is preferably a dendritic cell. Dendritic cells are immune cells forming part of the mammalian immune system. Their main function is to process antigenic material and present it on the surface to other cells of the immune system. Once activated, they migrate to the lymph nodes where they interact with T cells and B cells to initiate the adaptive immune response.

Dendritic cells are derived from hematopoietic bone marrow progenitor cells. These progenitor cells initially transform into immature dendritic cells which are characterized by high endocytic activity and low T-cell activation potential. Once they have come into contact with a presentable antigen, they become activated into mature dendritic cells and begin to migrate to the lymph node. Immature dendritic cells phagocytose pathogens and degrade their proteins into small pieces and upon maturation present those fragments at their cell surface using MHC molecules.

The dendritic cells may be derived from any appropriate source of dendritic cells, such as from the skin, inner lining of the nose, lungs, stomach and intestines or the blood. In a particularly preferred embodiment of the present invention the dendritic cells are derived from bone marrow.

Dendritic cells may be isolated from natural sources for use in the in vitro methods of the invention or may be generated in vitro. Dendritic cells arise from monocytes, i.e. white blood cells which circulate in the body and, depending on the right signal, can differentiate into either dendritic cells or macrophages. The monocytes in turn are formed from stem cells in the bone marrow. Monocyte-derived dendritic cells can be generated in vitro from peripheral blood mononuclear cells (PBMCs). Plating of PBMCs in a tissue culture flask permits adherence of monocytes. Treatment of these monocytes with interleukin 4 (IL-4) and granulocyte-macrophage colony stimulating factor (GM-CSF) leads to differentiation to immature dendritic cells (iDCs) in about a week. Subsequent treatment with tumour necrosis factor (TNF) further differentiates the iDCs into mature dendritic cells.

In another preferred aspect, the first cell (or cell which presents antigen in vivo) may be a macrophage.

The second cell as described herein is one to which a checkpoint inhibitor may bind. Such a cell may express a checkpoint molecule, e.g. a checkpoint protein or lipid, or its receptor or ligand, to which the checkpoint inhibitor may bind. As used herein reference to binding by the checkpoint inhibitor refers to making a specific binding interaction e.g. to a binding partner, e.g. an antibody to a target molecule containing a relevant epitope present on the second cell. The first and second cell may be a single cell, e.g. both be able to express an antigenic molecule or part thereof on its surface and bind a checkpoint inhibitor. Conveniently, however, they are separate cells. In this case, in a preferred feature, the second cell is a cell of the immune system, especially preferably a T or B cell and is preferably a cell which specifically recognizes the antigenic molecule or part thereof once expressed on the first cell. Whilst not wishing to be bound by theory, it is believed that in this method in which a first and second cell is used the first cell expresses the antigenic molecule or part thereof and the second cell is stimulated by said expression on said first cell wherein the stimulation is enhanced by the use of the checkpoint inhibitor. When only a single cell is used, the resultant cell has an enhanced ability to activate an immune response or is more susceptible to the immune response.

As used herein "contacting" refers to bringing the different components, e.g. the first cell and the photosensitizing agent and/or the antigenic molecule (and optionally the TLR ligand); or the second cell and the checkpoint inhibitor; as defined herein into physical contact with one another under conditions appropriate for internalization into the cells and/or binding of the checkpoint inhibitor, e.g. preferably at 37° C. in an appropriate nutritional medium, e.g. from 25-39° C. or in vivo at body temperature, i.e. 36-38° C. Similarly, the first and second cells (when different) may be contacted with one another to allow interaction between those cells, e.g. stimulation of the second cell by the first cell presenting the antigenic molecule. This contact may occur throughout the method or may occur for only portions of the method, e.g. after irradiation has occurred.

In vitro when using a first and second cell, various different combinations and timings may be used. Thus, for example, all the different agents and cells may be contacted with one another during the method or the cells and/or agents may be added at different times. As referred to herein, when "at least" the first or second cell is contacted with one or more agents, the first or second cell must be present, but in addition, the other cell may also be present. The first cell is contacted with at least the photosensitizing agent and the antigenic molecule (and optionally the checkpoint inhibitor) and the second cell is contacted with at least the checkpoint inhibitor. This may be achieved in separate containers or the required components may be added together. When the first and second cell are a single cell the various agents are all added to the same cell, but the order of addition may vary.

Thus, the first cell may be contacted with the photosensitizing agent and antigenic molecule (and optionally the TLR ligand) as defined herein sequentially or simultaneously. Optionally the checkpoint inhibitor may also be contacted with the first cell. Preferably, and conveniently one or more of the components are contacted with the first cell simultaneously (e.g. separately or together). For example at least the photosensitising agent and antigenic molecule (and optionally the TLR ligand) may be contacted with the cell simultaneously and the checkpoint inhibitor may also be added simultaneously or may be added before or after those components (with or without the addition of a second cell when the second cell is not the same as the first cell). The photosensitizing agent and antigenic molecule (and optionally the checkpoint inhibitor and/or the TLR ligand, when used) may be taken up by the cell into the same or different intracellular compartments (e.g. they may be co-translocated).

The cells are exposed to light of suitable wavelengths to activate the photosensitizing compound which in turn leads to the disruption of the intracellular compartment membranes. Conveniently this is performed after addition of the antigenic molecule and the photosensitizing agent to the first cell, but may also be performed after that addition.

WO 02/44396 (which is incorporated herein by reference) describes a method in which the order of the steps in the method may be arranged such that for example the photosensitizing agent is contacted with the cells and activated by irradiation before the molecule to be internalised (in this case the antigenic molecule) is brought into contact with the cells. This method takes advantage of the fact that it is not necessary for the molecule to be internalised to be present in the same cellular subcompartment as the photosensitizing agent at the time of irradiation.

Thus in one embodiment, said photosensitizing agent and/or said antigenic molecule (and optionally the checkpoint inhibitor and/or TLR ligand, when used) as defined herein are applied to the first cell together, or separately relative to one another. Irradiation is then performed at a time when at least the photosensitizing agent and the antigenic molecule appear in the same intracellular compartment. This is referred to as a "light after" method.

In an alternative embodiment, said method can be performed by contacting said first cell with the photosensitizing agent first, followed by contact with the antigenic molecule (and optionally the checkpoint inhibitor and/or TLR ligand, when used) as defined herein, and irradiation is performed after uptake of the photosensitizing agent into an intracellular compartment, but prior to the cellular uptake of the antigenic molecule (and optionally the checkpoint inhibitor and/or the TLR ligand, when used) into an intracellular compartment containing said photosensitizing agent (e.g. it may be present in a different intracellular compartment at the time of light exposure), preferably prior to cellular uptake into any intracellular compartment, e.g. prior to any cellular uptake. Thus for example the photosensitizing agent may be administered followed by irradiation and then administration of the remaining agents. This is the so-called "light before" method.

"Internalisation" as used herein, refers to the intracellular, e.g. cytosolic, delivery of molecules. In the present case "internalisation" may include the step of release of molecules from intracellular/membrane bound compartments into the cytosol of the cells.

As used herein, "cellular uptake" or "translocation" refers to one of the steps of internalisation in which molecules external to the cell membrane are taken into the cell such that they are found interior to the outer lying cell membrane, e.g. by endocytosis or other appropriate uptake mechanisms, for example into or associated with intracellular membrane-restricted compartments, for example the endoplasmic reticulum, Golgi body, lysosomes, endosomes etc.

The step of contacting the cell(s) with the various agents may be carried out in any convenient or desired way. Thus, if the contacting step is to be carried out in vitro the cell(s) may conveniently be maintained in an aqueous medium, such as for example appropriate cell culture medium, and at the appropriate time point the various agents can simply be added to the medium under appropriate conditions, for example at an appropriate concentration and for an appropriate length of time. For example, the cell(s) may be contacted with the agents in the presence of serum-free medium, or with serum-containing medium.

The comments below discuss the application of the various agents to the cell(s) separately. As discussed above, however, these agents may be applied to cell(s) together, separately, simultaneously or sequentially. As referred to herein, the application of the various agents used in the methods of the invention may be to cells in vitro or in vivo. In the latter case, the application may be via direct (i.e. localized) or indirect (i.e. systemic or non-localized) administration as described in more detail hereinbelow.

The photosensitizing agent is brought into contact with the cell(s) (or subject to be treated in which such cells are present) at an appropriate concentration and for an appropriate length of time which can easily be determined by a skilled person using routine techniques, and will depend on such factors as the particular photosensitizing agent used and the target cell type and location. The concentration of the photosensitizing agent is conveniently such that once taken up into the cell, e.g. into, or associated with, one or more of its intracellular compartments and activated by irradiation, one or more cell structures are disrupted e.g. one or more intracellular compartments are lysed or disrupted. For example photosensitizing agents as described herein may be used at a concentration of, for example, 10 to 50 µg/ml.

For in vitro use the range can be much broader, e.g. 0.0005-500 µg/ml. For in vivo human treatments the photosensitizing agent may be used in the range 0.05-20 mg/kg body weight when administered systemically. Alternatively, a range of 0.005-20 mg/kg body weight may be used for systemic administration. More conveniently the photosensitizing agent is administered locally, for example by intradermal, subcutaneous or intratumoural administration, and in that case the dose may be in the region of 1-5000 µg, for example 10-2500, 25-1000, 50-500, 10-300 or 100-300 µg. Preferably the dose is selected from 25 µg, 50 µg, 100 µg, 150 µg, 200 µg and 250 µg. Preferably the dose is 75-125 µg, e.g. 100 µg. The doses provided are for a human of average weight (i.e. 70 kg). For intradermal injection the photosensitiser dose may be dissolved in 100 µl-1 ml, i.e. the concentration may be in the range of 1-50000 µg/ml. In smaller animals the concentration range may be different and can be adjusted accordingly though when administered locally, little variation in dosing is necessary for different animals.

The concentration of antigen to be used will depend on the antigen which is to be used. Conveniently a concentration of 0.001-500 µg/ml (e.g. 20-500, 20-300, 20-100 µg/ml, 20-50, 10-50, 5-50, 1-50, 0.01-50, or 0.001-50 µg/ml) antigen may be used in vitro. For a peptide antigen a lower concentration e.g. of 0.001-500, e.g. 0.001-1, 5, 25, 50 or 100 µg/ml may be used. For a protein antigen a higher concentration of e.g. 0.5-500 µg/ml may be used. For in vivo use the protein antigen dose may be in the range 0.5-500 µg, for example 10-100 µg or 10-200 µg. For peptide antigens an in vivo dose of 0.1-4000 µg, e.g. 0.1-2000 µg, 0.1-1000 µg or 0.1-500 µg, for example 0.1-200 µg, may be employed. Such doses are appropriate for local administration. The above concentrations may apply to the total antigen used or each antigen used when the antigenic molecule is comprised of more than one antigen. An appropriate concentration can be determined depending on the efficiency of uptake of the agent in question into the cells in question and the final concentration it is desired to achieve in the cells.

The concentration of checkpoint inhibitor to be used will depend on the checkpoint inhibitor which is to be used. Conveniently a concentration of 0.001-500 µg/ml (e.g. 20-500, 20-300, 20-100 µg/ml, 20-50, 10-50, 5-50, 1-50, 0.01-50, or 0.001-50 µg/ml) may be used in vitro. For in vivo use the checkpoint inhibitor dose may be in the range 0.5-500 µg, for example 10-100 µg or 10-200 µg. In a preferred embodiment a dose of 100 µg or 200 µg may be used. Such doses are appropriate for local administration. For systemic, e.g. intravenous or intraperitoneal, administration the dose may be in the range of 0.1-45 mg/kg, e.g. 1-40, 5-35, 10-30 or 15-25 mg/kg, e.g. 5-10 mg/kg or 2-5 mg/kg, for example 3 mg/kg. The above concentrations may apply to the total checkpoint inhibitor used or each checkpoint inhibitor used when more than one checkpoint inhibitor is used.

An appropriate concentration can be determined depending on the efficiency of the checkpoint inhibitor in question, on the cells in question, and the final concentration it is desired to achieve in the cells.

The concentration of the TLR ligand as defined herein, when used, will also depend on the particular molecule which is to be used, and the skilled man will be aware of suitable concentrations or doses. The concentrations below may apply to the total TLR ligand used or each TLR ligand used when more than one TLR ligand is used.

Examples of suitable in vitro and in vivo concentrations or doses are shown in Table 2 below.

TABLE 2

| Ligand | In vitro concentration | In vivo dosage (preferably for local administration) |
| --- | --- | --- |
| LPS | 0.001-100 µg/ml | 0.1-100 µg |
| Flagellin | 1-100 µg/ml | 1-200 µg |
| Poly(IC) | 0.01-100 µg/ml | 1 µg-5 mg (or to 10 mg) (e.g. 10 µg-5 mg) |
| ssPolyU | 1-10 000 ng/ml | 10 µg-5 mg |
| MPLA | 1-10 000 ng/ml | 2-500 µg |
| Imidazoquinolines | 0.01-100 µg/ml | 10-1000 µg (or to 10 mg), e.g. 20-100 µg in mice and 10 µg-10 mg in humans |
| CpG ODNs | 1-100 µg/ml | 10-1000 µg (or to 10 mg) e.g. 20-100 µg in mice and 10 µg-10 mg in humans |

Thus, for example, conveniently a concentration of 1-100 µg/ml (e.g. 20-100 µg/ml, or 20-50 µg/ml) may be used in vitro. In vivo doses of 10-1000 µg of the imidazoquinoline compound may be used, for example 20-100 µg in a mouse, and in humans 10 µg-10 mg may be employed. For topical administration of e.g. imiquimod in humans, a dose of 2.5-50 mg, e.g. at 1-5 mg/cm$^2$, e.g. 2.5 mg/cm$^2$, may be used. For resiquimod the dose may be 0.1-50 mg, e.g. 1-5 mg, e.g. at 1-5 mg/cm$^2$. A similar dose is suitable for gardiquimod. For intradermal injection of the imidazoquinoline compound a smaller dose may be used, for example at least 10 µg or 50 µg, e.g. 10 µg-1 mg could be used. Similar doses may be used for the CpG oligonucleotide and other TLR ligands. Poly(IC) may be administered at an in vivo dose of 1-100 µg in mice (e.g. 5 µg or 10 µg) and 1 µg-10 mg in humans.

In most cases the photosensitizing agent, the antigenic molecule (and optionally the checkpoint inhibitor and/or the TLR ligand when used) as defined herein are administered together, but this may be varied. Thus different times or modes or sites of administration (or contact with the cell) are contemplated for each of the different components and such methods are encompassed within the scope of the invention as described herein.

In one embodiment, particularly in the in vivo methods and uses of the invention, the photosensitising agent, antigenic molecule (and the TLR ligand when used) are administered together and separately from the checkpoint inhibitor. The separate administration may be simultaneous (e.g. when used in vivo via different administration routes) or may be consecutive. In one in vivo example, the checkpoint inhibitor may be administered on multiple occasions, relative to the other agents, e.g. in the course of treatment may be administered 3, 4, 5, or 6 or more times relative to the other agents which may be administered e.g. 1, 2 or 3 times. The method of the invention encompasses methods in which illumination in the PCI method occurs after (or shortly before to allow internalisation into relevant compartments post-illumination) all relevant agents have contacted the cell (or been administered in vivo). Thus, the checkpoint inhibitor may be administered separately from the other components, e.g. in a separate formulation. If more than one checkpoint inhibitor (or antigen or TLR ligand) is used, the different checkpoint inhibitors (antigen or TLR ligands) may be administered separately, simultaneously or sequentially relative to one another.

In one embodiment in which a TLR ligand is used in the method, the TLR ligand, for example a CpG oligonucleotide or an imidazoquinoline compound, an LPS or a poly(IC) molecule as defined herein is administered separately from the antigen, for example in a separate formulation, e.g. a cream or gel, or systemically, e.g. via oral administration (for example with resiquimod). Thus, in one embodiment the TLR ligand, e.g. a CpG oligonucleotide or imidazoquinoline compound may be administered prior to administration of the antigen and/or photosensitiser, for example 24 hours before, e.g. by local (topical) pretreatment. In some cases the TLR ligand, e.g. Poly(IC) or LPS is administered before, with, or after, the antigenic molecule.

The TLR ligand may be administered separately relative to the other agents, e.g. approximately 2 hours prior to illumination. In an alternative embodiment the agent may be administered with, or at the same time, i.e. simultaneously, as the antigen. The checkpoint inhibitor (and preferably all of the agents described for use in the methods) is preferably administered within 120, 72 hours, preferably within 48, 24, 12, 6, 4, 2, 1 hour, 30 or 15 minutes of the illumination (i.e. either before or after the illumination).

The contact between the cell (first or second, as appropriate, or relevant equivalent cell in vivo) and the photosensitizing agent and/or antigenic molecule and/or the checkpoint inhibitor (and the TLR ligand when used) as defined herein is conveniently from 15 minutes to 24 hours, e.g. 30 minutes to four hours, preferably from 1.5 to 2.5 hours. Alternatively, the range of time may be from about 1 hour to about 48 hours, for example from about 2 hours to about 40 hours, or from about 6 hours to about 36 hours, e.g. from 12 hours to 30 hours, e.g. 16 hours to 20 hours, for example 18 hours or about 18 hours.

In a preferred embodiment the initial incubation of the first cell (or equivalent cell in vivo) is with the photosensitising agent. In one embodiment the time between the administration of the photosensitizing agent and the antigenic molecule (and optionally checkpoint inhibitor and/or the TLR ligand, when used) is a matter of hours. For example, the photosensitizing agent may be applied 16 to 20 hours, e.g. 18 hours, before illumination, and the antigenic molecule (and optionally checkpoint inhibitor and/or the TLR ligand, when used) may be applied 1 to 3 hours, e.g. 2 hours before illumination. Thus, the time between the administration of the photosensitizing agent and the antigenic molecule (and optionally the checkpoint inhibitor and/or the TLR ligand, when used) may be in the range of 15 to 23 hours.

Thus, the first cell (or in vivo equivalent) is then incubated with the antigen (and optionally the checkpoint inhibitor and/or the TLR ligand, when used) as defined herein after the incubation with the photosensitiser. Conveniently the cells may be placed into photosensitizer/antigen-free medium after the contact with the photosensitizer/antigen and before irradiation, e.g. for 30 minutes to 4 hours, e.g. from 1.5 to 2.5 hours, depending on the timing of the incubation with the photosensitiser and antigenic molecule and (optionally the checkpoint inhibitor and/or the TLR ligand, when used).

Similar considerations apply to the contact times for the second cell with the checkpoint inhibitor (and other agents when present) if the second cell is not also the first cell. Thus, for example, the second cell may be contacted with the checkpoint inhibitor for the above indicated times, though irradiation of said second cell may not necessarily occur if treated separately to the first cell.

In vivo an appropriate method and time of incubation by which the various agents are brought into contact with the target cells will be dependent on factors such as the mode of administration and the type of agents which are used. For example, if the agents are injected into a tumour, tissue or organ which is to be treated/irradiated, the cells near the injection point will come into contact with and hence tend to take up, or bind to, one or more of the agents more rapidly than the cells located at a greater distance from the injection point, which are likely to come into contact with the agents at a later time point and lower concentration. Conveniently a time of 6-24 hours may be used.

In addition, agents administered by intravenous injection or orally may take some time to arrive at the target cells and it may thus take longer post-administration e.g. several days, in order for a sufficient or optimal amount of the agents to accumulate in and/or on a target cell or tissue. The time of administration required for individual cells in vivo is thus likely to vary depending on these and other parameters.

Nevertheless, although the situation in vivo is more complicated than in vitro, the underlying concept of the present invention is still the same, i.e. the time at which the molecules come into contact with the target cells must be such that before irradiation occurs an appropriate amount of the photosensitizing agent has been taken up by the target cells and either: (i) before or during irradiation the antigenic molecule (and optionally the checkpoint inhibitor and/or the TLR ligand when used) has either been taken up, or will be taken up after sufficient contact with the target cells, into the cell, for example into the same or different intracellular compartments relative to the photosensitizing agent or (ii) after irradiation the antigenic molecule (and optionally the checkpoint inhibitor and/or the TLR ligand when used) is in contact with the cells for a period of time sufficient to allow its uptake into the cells. Similarly the contact of the checkpoint inhibitor with the target cells must be such that binding of the checkpoint inhibitor can occur and this binding should preferably be complete by the time the cells which have taken up the antigenic molecules are presenting that molecule or a part thereof on the cell's surface.

For administration of agents described herein in vivo, any mode of administration common or standard in the art may be used, e.g. injection, infusion, topical administration, transdermal administration, both to internal and external body surfaces etc. For in vivo use, the invention can be used in relation to any tissue which contains cells to which the photosensitising agent containing compound or antigenic molecule is localized, including body fluid locations, as well as solid tissues. All tissues can be treated as long as the photosensitiser is taken up by the target cells, and the light can be properly delivered. Preferred modes of administration, for example for the photosensitising agent (and/or the antigenic molecule and the TLR ligand, when used) are intradermal, subcutaneous, topical or intratumoural administration or injection, preferably said administration is by intradermal injection or intratumoural injection. For the checkpoint inhibitor administration may be, for example, by systemic, e.g. intravenous, administration, or by intratumoural administration. In the alternative, as demonstrated in the Examples, intraperitoneal administration may be used.

To achieve the desired outcome, e.g. antigen presentation, generation of an immune response or vaccination, the methods or parts thereof may be repeated, e.g. "re-vaccination" may take place. Thus, the method in its entirety may be performed multiple times (e.g. 2, 3 or more times) after an appropriate interval or parts of the method may be repeated, e.g. further administration of the checkpoint inhibitor (and/or the TLR ligand when used) as defined herein or additional irradiation steps. For example, the method or part of the method may be performed again a matter of days, e.g. between 5 and 60 days (for example 7, 14, 15, 21, 22, 42 or 51 days), e.g. 7-20 days, preferably 14 days, or weeks, e.g. between 1 and 5 weeks (for example, 1, 2, 3 or 4 weeks) after it was first performed. All or part of the method may be repeated multiple times at appropriate intervals of time, e.g. every two weeks or 14 days. In a preferred embodiment the method is repeated at least once. In another embodiment the method is repeated twice.

In one embodiment, in addition to performing the method multiple times, the checkpoint inhibitor may additionally be administered separately, e.g. before or after each performance of the method, e.g. 1, 2 or 3 or more times, e.g. as described in the Examples.

In an alternative embodiment, parts of the method of the invention may be carried out prior to the method of the invention being carried out. For example, the method may be carried out one or more times, for example twice, in the absence of checkpoint inhibitor before the method of the invention is carried out. Alternatively, the method may be carried out one or more times, for example twice, in the absence of photosensitiser and illumination (and optionally TLR ligand) before the method of the invention is carried out. Part of the method may be carried out a matter of days, e.g. 7 or 14 days, or weeks, e.g. 1, 3 or 4 weeks before the method of the invention is carried out. Part of the method may be repeated one or more times at these time intervals before the method of the invention is carried out. Thus, in a preferred aspect, the antigenic molecule is administered (e.g. to the subject) equal to or greater than 2 times (e.g. at the time intervals discussed above), wherein at least the administration of said antigenic molecule is performed in accordance with the method of the invention.

Alternatively described, the invention provides a method as described herein using an antigenic molecule, photosensitising agent and optionally a TLR ligand (but not a checkpoint inhibitor) which method is performed in conjunction with administration (cell contact) with a checkpoint inhibitor (one or more times) and said method may be performed in line with the preferred embodiments and for the methods and uses and products for use as described herein.

"Irradiation" to activate the photosensitising agent refers to the administration of light directly or indirectly as described hereinafter. Thus subjects or cells may be illuminated with a light source for example directly (e.g. on single cells in vitro) or indirectly, e.g. in vivo when the cells are below the surface of the skin or are in the form of a layer of cells not all of which are directly illuminated, i.e. without the screen of other cells. Illumination of the cell or subject may occur approximately 18-24 hours after administration of the photosensitizing agent, antigenic molecule (and optionally the checkpoint inhibitor and/or the TLR ligand, when used) as defined herein.

The light irradiation step to activate the photosensitising agent may take place according to techniques and procedures well known in the art. The wavelength of light to be used is selected according to the photosensitising agent to be used. Suitable artificial light sources are well known in the art, e.g. using blue (400-475 nm) or red (620-750 nm) wavelength light. For $TPCS_{2a}$ for example a wavelength of between 400 and 500 nm, more preferably between 400 and 450 nm, e.g. from 430-440 nm, and even more preferably approximately 435 nm, or 435 nm may be used. Where appropriate the photosensitiser, e.g. a porphyrin or chlorin, may be activated by green light, for example the KillerRed (Evrogen, Moscow, Russia) photosensitizer may be activated by green light.

Suitable light sources are well known in the art, for example the LumiSource® lamp of PCI Biotech AS. Alternatively, an LED-based illumination device which has an adjustable output power of up to 60 mW and an emission spectra of 430-435 nm may be used. For red light, a suitable source of illumination is the PCI Biotech AS 652 nm laser system SN576003 diode laser, although any suitable red light source may be used.

The time for which the cells are exposed to light in the methods of the present invention may vary. The efficiency of the internalisation of a molecule into the cytosol increases with increased exposure to light to a maximum beyond which cell damage and hence cell death increases.

A preferred length of time for the irradiation step depends on factors such as the target, the photosensitizer, the amount of the photosensitizer accumulated in the target cells or tissue and the overlap between the absorption spectrum of the photosensitizer and the emission spectrum of the light source. Generally, the length of time for the irradiation step is in the order of seconds to minutes or up to several hours (even up to 12 hours), e.g. preferably up to 60 minutes e.g. from 0.25 or 1 to 30 minutes, e.g. from 0.5 to 3 minutes or from 1 to 5 minutes or from 1 to 10 minutes e.g. from 3 to 7 minutes, and preferably approximately 3 minutes, e.g. 2.5 to 3.5 minutes. Shorter irradiation times may also be used, for example 1 to 60 seconds, e.g. 10-50, 20-40 or 25-35 seconds.

Appropriate light doses can be selected by a person skilled in the art and again will depend on the photosensitizer used and the amount of photosensitizer accumulated in the target cells or tissues. The light doses are usually lower when photosensitizers with higher extinction coefficients (e.g. in the red area, or blue area if blue light is used, depending on the photosensitiser used) of the visible spectrum are used. For example, a light dose in the range of 0.24-7.2 $J/cm^2$ at a fluence range of 0.05-20 $mW/cm^2$, e.g. 2.0 $mW/cm^2$, may be used when an LED-based illumination device which has an adjustable output power of up to 60 mW and an emission spectra of 430-435 nm is employed. Alternatively, e.g. if the LumiSource® lamp is employed a light dose in the range of 0.1-6 $J/cm^2$ at a fluence range of 0.1-20 (e.g. 13 as provided by Lumisource®) $mW/cm^2$ is appropriate. For red light, a light dose of 0.03-1 $J/cm^2$, e.g. 0.3 $J/cm^2$, at a fluence range of 0.1-5 $mW/cm^2$, e.g. 0.81 $mW/cm^2$, may be used.

Furthermore, if cell viability is to be maintained, the generation of excessive levels of toxic species is to be avoided and the relevant parameters may be adjusted accordingly.

The methods of the invention may inevitably give rise to some cell damage by virtue of the photochemical treatment i.e. by photodynamic therapy effects through the generation of toxic species on activation of the photosensitizing agent. Depending on the proposed use, this cell death may not be of consequence and may indeed be advantageous for some applications (e.g. cancer treatment). In most embodiments, however, cell death is avoided to allow the generation of an immune response from the presenting cell. The methods of the invention may be modified such that the fraction or proportion of the surviving cells is regulated by selecting the light dose in relation to the concentration of the photosensitizing agent. Again, such techniques are known in the art.

Preferably, substantially all of the cells, or a significant majority (e.g. at least 75%, more preferably at least 80, 85, 90 or 95% of the cells) are not killed. In vitro cell viability following PCI treatment can be measured by standard techniques known in the art such as the MTS test. In vivo cell death of one or more cell types may be assessed within a 1 cm radius of the point of administration (or at a certain depth of tissue), e.g. by microscopy. As cell death may not occur instantly, the % cell death refers to the percent of cells which remain viable within a few hours of irradiation (e.g. up to 4 hours after irradiation) but preferably refers to the % viable cells 4 or more hours after irradiation.

The method described herein may be performed in vivo, in vitro or ex vivo. Preferably the method is used in vitro or ex vivo to generate cells for administration in vivo or the method is used in vivo. Thus in a preferred feature, the method may be used to generate an immune response in a subject.

As described hereinbefore, in a preferred aspect the invention provides a method of generating an immune response in a subject, comprising administering to said subject an antigenic molecule, a photosensitizing agent, a checkpoint inhibitor and optionally a TLR ligand as defined hereinbefore, and irradiating said subject with light of a wavelength effective to activate said photosensitizing agent, wherein an immune response is generated.

An "immune response" which may be generated may be humoral and cell-mediated immunity, for example the stimulation of antibody production, or the stimulation of cytotoxic or killer cells, which may recognise and destroy (or otherwise eliminate) cells expressing "foreign" antigens on their surface. The term "stimulating an immune response" thus includes all types of immune responses and mechanisms for stimulating them and encompasses stimulating CTLs which forms a preferred aspect of the invention. Preferably the immune response which is stimulated is cytotoxic CD8 T cells. The extent of an immune response may be assessed by markers of an immune response, e.g. secreted molecules such as TNF-α or IFNγ or the production of antigen specific T cells (e.g. assessed as described in the Examples).

The stimulation of cytotoxic cells or antibody-producing cells, requires antigens to be presented to the cell to be stimulated in a particular manner by the antigen-presenting cells, for example MHC Class I presentation (e.g. activation of $CD8^+$ cytotoxic T-cells requires MHC-I antigen presentation). Preferably the immune response is stimulated via MHC-I presentation.

Preferably the immune response is used to treat or prevent a disease, disorder or infection, e.g. a condition involving aberrant cell proliferation, e.g. cancer or an infection such as a viral infection such as hepatitis. Thus, in a further preferred embodiment the present invention provides a method of treating cancer, comprising administering to said subject an antigenic molecule, a photosensitizing agent, a checkpoint inhibitor, and irradiating said subject with light of a wavelength effective to activate said photosensitizing agent, wherein an immune response is generated.

In one embodiment the cancer is melanoma. Melanoma is a malignant tumour of melanocytes, which are the cells responsible for producing melanin, the dark pigment responsible for skin colour. These cells occur predominantly in the skin, but are also found in other parts of the body, including the bowel and the eye. Melanoma can originate in any part of the body that contains melanocytes.

"Melanoma" as referred to herein includes all types of melanoma, including for example superficial spreading melanoma, nodular melanoma, lentigo maligna melanoma, desmoplastic melanoma, acral lentiginous melanoma and amelanotic melanoma, polypoid melanoma, melanoma with small nevus-like cells and melanoma with features of a Spitz nevus.

Whilst the majority of melanomas occur cutaneously (cutaneous malignant melanoma), melanoma can also occur elsewhere in the body, for example in the internal organs, e.g. in the mucosal membranes. Clear cell sarcoma is a malignant melanoma of the soft tissues. Melanoma can also occur in the eye (uveal melanoma), vulva, vagina or rectum. These melanomas are also included in the scope of the invention. Preferably the melanomas to be treated are skin melanomas. Melanoma also extends to metastatic melanoma, i.e. cells that have originated from a primary melanoma but which have metastasised to a different location to yield secondary tumours. Treatment or prevention of melanoma as described herein extends to treatment of primary melanomas and/or secondary tumours deriving from the primary melanoma. As such, the invention also has utility in treating metastatic melanoma.

In an alternative embodiment, the cancer is associated with or caused/induced by a papillomavirus, particularly a human papillomavirus (HPV). As discussed above, the papillomavirus genome is divided into an early region (E), encoding six (E1, E2, E4, E5, E6, and E7) open reading frames (ORF) that are expressed immediately after initial infection of a host cell, and a late region (L) encoding a major capsid protein L1 and a minor capsid protein L2. All viral ORFs are encoded on one DNA strand. The HPV antigen which may be used according to the invention, which can be associated with cancers resulting from HPV infection, can be one or more known antigenic peptide or T-cell epitope as discussed herein. As discussed above, there are several types of HPV, and the cancer associated with HPV according to the present invention may be associated with, or result from, any type of HPV, for example HPV-16 and/or HPV-18, or HPV-31 or HPV-45. The antigen to be used according to the invention may be derived from any of the E1, E2, E4, E5, E6 or E7 proteins or any of the L1 and L2 proteins. Thus, the antigenic molecule may be derived from one or more of the E2, E6, and E7 proteins of HPV-16 and 18. In a preferred embodiment the antigenic molecule contains the HPV-16 E7 sequence GQAEPDRAHYNIVTFCCKCDSTLRLCVQSTHVDIR (the CD8 epitope is shown in bold). Thus, the HPV antigen may be a 35 amino acid peptide. Alternatively, the antigenic molecule may be only the CD8 epitope RAHYNIVTF, i.e. a shorter peptide.

In an alternative embodiment, the disease, disorder or infection is a viral infection, preferably a papillomavirus infection, particularly a human papillomavirus (HPV) infection.

Preferably the method is used for vaccination. As referred to herein, "vaccination" is the use of an antigen (or a molecule containing an antigen) to elicit an immune response which is prophylactic or therapeutic against the development (or further development) of a disease, disorder or infection, wherein that disease, disorder or infection is associated with abnormal expression or presence of that antigen. Preferably the disease is cancer, for example melanoma or a cancer associated with a papillomavirus such as HPV. In one embodiment the vaccination is therapeutic, for example in the treatment of cancers discussed herein. In an alternative embodiment the vaccination is prophylactic, for example to prevent a cancer or to reduce further cancers developing following treatment of an earlier cancer with a therapeutic vaccination. In a further embodiment when an immune response to an infection is to be generated, e.g. a viral infection such as HPV infection, the vaccination is prophylactic in nature.

In a preferred embodiment of the present invention, the subject of the method, e.g. vaccination, is a mammal, preferably a cat, dog, horse, donkey, sheep, pig, goat, cow, mouse, rat, rabbit or guinea pig, but most preferably the subject is a human.

Preferably the methods described herein achieve synergy, i.e. the extent of cell surface presentation or the immune response generated is enhanced more than the combined enhancement observed by (i) performing the method with the antigenic molecule and photosensitizing agent (and illumination) in the absence of the checkpoint inhibitor (and the TLR ligand) and (ii) performing the method with the antigenic molecule and the checkpoint inhibitor (and optionally the TLR ligand) in the absence of the photosensitizing agent and/or the irradiation step, i.e. synergy between the methods is observed. The level of cell surface presentation or immune response generation may be assessed by appropriate means, e.g. number of antigen-specific CD8+ cells or levels of markers of immune response activation, e.g. IFNγ or TNFα.

"Synergy" as used to herein refers to a quantitative improvement over merely additive effects.

The various agents used in the methods of the invention may be administered to the subject separately, sequentially or simultaneously.

Aspects and features discussed above in relation to the method of expressing an antigenic molecule or a part thereof on the surface of a cell of the present invention, where appropriate, are also applicable to the method of generating an immune response above and vice versa.

The invention also provides a method for introducing an antigenic molecule into the cytosol of a cell, comprising
a) providing a first cell on which said antigenic molecule or part thereof is to be expressed and a second cell to which a checkpoint inhibitor may bind, wherein said first and second cell may be the same cell or different cells,
b) contacting at least said first cell with said antigenic molecule, a photosensitizing agent, and optionally a TLR ligand,
c) contacting at least the second cell with a checkpoint inhibitor, and
d) irradiating at least the first cell with light of a wavelength effective to activate the photosensitising agent, wherein said antigenic molecule is released into the cytosol of the cell and the antigenic molecule or a part thereof is subsequently presented on the surface of the first cell,
wherein said first and second cells are contacted with one another before, during and/or after said irradiation. Once activated, intracellular compartments within said cell containing said compound release the molecule contained in these compartments into the cytosol.

The methods of the invention above may be used in vitro or in vivo, for example either for in situ treatment or for ex vivo treatment followed by the administration of the treated cells to the body.

The invention further provides a cell expressing an antigenic molecule, or a part thereof, on its surface, or a population thereof, which cell is obtainable (or obtained) by any of the methods as defined herein. Also provided is the cell or cell population for use in prophylaxis, or therapy, as described hereinafter.

The cell population may be provided in a pharmaceutical composition comprising in addition one or more pharmaceutically acceptable diluents, carriers or excipients.

The present invention also provides a pharmaceutical composition comprising an antigenic molecule, a photosensitizing agent, a checkpoint inhibitor and optionally a TLR ligand as defined herein and one or more pharmaceutically acceptable diluents, carriers or excipients.

These compositions (and products of the invention) may be formulated in any convenient manner according to techniques and procedures known in the pharmaceutical art, e.g. using one or more pharmaceutically acceptable diluents, carriers or excipients. "Pharmaceutically acceptable" as referred to herein refers to ingredients that are compatible with other ingredients of the compositions (or products) as well as physiologically acceptable to the recipient. The nature of the composition and carriers or excipient materials, dosages etc. may be selected in routine manner according to choice and the desired route of administration, purpose of treatment etc. Dosages may likewise be determined in routine manner and may depend upon the nature of the molecule (or components of the composition or product), purpose of treatment, age of patient, mode of administration etc. In connection with the photosensitizing agent, the potency/ability to disrupt membranes on irradiation, should also be taken into account.

The cells, for example antigen presenting cells, may be prepared in vitro. In treatment methods, these cells may be administered to a body in vivo or a body tissue ex vivo such that those cells may stimulate an immune response, e.g. for prophylactic or therapeutic purposes.

Thus the invention further provides a cell population (or composition containing the same) as defined herein, or an antigenic molecule, a photosensitizing agent, a checkpoint inhibitor and optionally a TLR ligand as defined herein, for use in prophylaxis or therapy or for use in stimulating an immune response, for example for vaccination purposes, e.g. for stimulating CTLs, in a subject, preferably for treating or preventing a disease, disorder or infection in said subject, particularly for treating or preventing cancer, such as melanoma or cancers associated with a papillomavirus such as HPV. Alternatively defined the present invention provides use of (i) a cell population, (ii) a composition as defined herein, or (iii) an antigenic molecule and/or a photosensitizing agent and/or a checkpoint inhibitor and optionally a TLR ligand, for the preparation of a medicament for use in stimulating an immune response (e.g. for stimulating CTLs) in a subject, preferably for treating or preventing a disease, disorder or infection in said subject, preferably for vaccination and/or for treating or preventing cancer, such as melanoma or cancers associated with a papillomavirus such as HPV, wherein preferably said immune response is stimulated by a method as defined herein.

Said stimulation, treatment or prevention preferably comprises administering said medicament to said subject.

The antigenic molecule, photosensitizing agent and the checkpoint inhibitor (and optionally a TLR ligand) may be combined and presented in a composition. Alternatively expressed, the invention provides use of an antigenic molecule and/or a photosensitizing agent and/or a checkpoint inhibitor and optionally a TLR ligand, when used, as defined herein in the manufacture of a medicament for stimulating an immune response (e.g. for stimulating CTLs in a subject), preferably to treat or prevent a disease, disorder or infection in said subject, particularly for vaccination purposes, wherein said medicament comprises a population of cells expressing an antigenic molecule or a part thereof on the surface of said cells obtainable by a method as defined herein, for administration to said subject. Preferably the cell population is obtained by such methods. The population is for administration to the subject.

In an alternative embodiment the present invention provides an antigenic molecule, photosensitizing agent and a checkpoint inhibitor and optionally a TLR ligand as defined herein for use in expressing said antigenic molecule or a part thereof on the surface of a cell to stimulate an immune response (e.g. for stimulating CTLs) in a subject, preferably to treat or prevent a disease, disorder or infection in said subject, wherein said use comprises a method as defined herein, preferably to prepare a population of cells, e.g. dendritic cells. These cells may then be administered to the subject.

The invention further provides a product comprising an antigenic molecule, photosensitizing agent, a checkpoint inhibitor and optionally a TLR ligand as defined herein as a combined preparation for simultaneous, separate or sequential use in stimulating an immune response in a subject (or for expressing an antigenic molecule or a part thereof on the surface of a cell or for internalising an antigenic molecule into the cytosol of a cell) in a method as defined herein, preferably to treat or prevent a disease, disorder or infection in a subject.

The present invention also provides a kit for use in stimulating an immune response in a subject, preferably for treating or preventing a disease, disorder or infection in said subject, for example for use in vaccination or immunisation, or for expressing an antigenic molecule or a part thereof on the surface of a cell or for internalising an antigenic molecule into the cytosol of a cell in a method as defined herein, said kit comprising a first container containing a photosensitizing agent as defined herein;

a second container containing said antigenic molecule as defined herein;

a third container containing a checkpoint inhibitor as defined herein; and optionally a fourth container containing a TLR ligand as described herein.

The products and kits of the invention may be used to achieve cell surface presentation (or therapeutic methods) as defined herein.

In a yet further embodiment the present invention provides a method of generating an immune response (e.g. for stimulating CTLs) in a subject, preferably to treat or prevent a disease, disorder or infection in said subject, comprising preparing a population of cells according to the method defined herein, and subsequently administering said cells to said subject.

The antigenic presentation achieved by the claimed invention may advantageously result in the stimulation of an immune response when the treated cells are administered in vivo. Preferably an immune response which confers protection against subsequent challenge by an entity comprising or containing said antigenic molecule or part thereof is generated, and consequently the invention finds particular utility as a method of vaccination.

The disease, disorder or infection is any disease, disorder or infection which may be treated or prevented by the generation of an immune response, e.g. by eliminating abnormal or foreign cells which may be identified on the basis of an antigen (or its level of expression) which allows discrimination (and elimination) relative to normal cells. Selection of the antigenic molecule to be used determines the disease, disorder or infection to be treated. Based on the antigenic molecules discussed above, the methods, uses, compositions, products, kits and so forth, described herein may be used to treat or prevent against, for example, infections (e.g. viral or bacterial as mentioned hereinbefore), cancers or multiple sclerosis. Prevention of such diseases, disorders or infection may constitute vaccination.

As defined herein "treatment" refers to reducing, alleviating or eliminating one or more symptoms of the disease, disorder or infection which is being treated, relative to the symptoms prior to treatment. Said treatment may comprise reduction in the size or volume of a tumour in the case of treating a cancer or reducing the number of aberrant cells when treating aberrant cell proliferation. "Prevention" (or prophylaxis) refers to delaying or preventing the onset of the symptoms of the disease, disorder or infection. Prevention may be absolute (such that no disease occurs) or may be effective only in some individuals or for a limited amount of time.

For in vivo administration of the cells, any mode of administration of the cell population which is common or standard in the art may be used, e.g. injection or infusion, by an appropriate route. Conveniently, the cells are administered by intralymphatic injection. Preferably $1 \times 10^4$ to $1 \times 10^8$ cells are administered per kg of subject (e.g. $1.4 \times 10^4$ to $2.8 \times 10^6$ per kg in human). Thus, for example, in a human, a dose of $0.1\text{-}20 \times 10^7$ cells may be administered in a dose, i.e. per dose, for example as a vaccination dose. The dose can be repeated at later times if necessary.

The invention will now be described in more detail in the following non-limiting Examples with reference to the following drawings in which.

EXAMPLES

Example 1

The study was performed to investigate the effect of PCI in combination with the checkpoint inhibitors anti-CTLA4 and anti-PD-1 in the TC-1 mouse model for HPV-induced cancer.

Materials and Methods

Mice

C57BL/6 mice were purchased from Harlan (Horst, The Netherlands). All mice were kept under specified pathogen-free (SPF) conditions, and the procedures performed were approved by Swiss Veterinary authorities.

Tumour Inoculation

Mice were inoculated subcutaneously on their right flank with 200,000 TC-1 tumour cells (licensed from The Johns Hopkins University, 3400 N. Charles St., Baltimore, Md. 21218-2695) on day 0.

Immunisation Protocol

The further treatment schedule is outlined in Table 3. The checkpoint inhibitors anti-CTLA4 and anti-PD-1 were administered by intraperitoneal injection at the time points shown in Table 3. The doses of the checkpoint inhibitors were 100 μg per injection for anti-CTLA4, and 200 μg for anti-PD-1. Both checkpoint inhibitors were obtained from Bio X Cell, 10 Technology Drive, Suite 2B, West Lebanon, NH03784-1671, USA (mAb anti m CTLA-4, catalog 13E0131 and mAb anti m PD-1, catalog BE0146).

TABLE 3

| Day | | Checkpoint inhibitor administration (i.p.) |
|---|---|---|
| 0 | Tumour inoculation | |
| 5 | 1st immunisation | x |
| 6 | 1st illumination | |
| 10 | | x |
| 13 | | x |
| 17 | | x |
| 20 | 2nd immunisation | x |
| 21 | 2nd illumination | |
| 24 | | x |
| 27 | | x |
| 31 | | |

Each immunisation was performed by intradermal administration of a mixture of different combinations of 50 μg HPV long peptide antigen GQAEPDRAHYNIVTFCCK-CDSTLRLCVQSTHVDIR (United Peptides (Herndon, Va.), 25 μg $TPCS_{2a}$ (Amphinex, PCI Biotech AS) (for the animals receiving PCI treatment) and 5 μg high molecular weight Polyinosinic-polycytidylic acid (Poly(IC)) (Invivo-Gen (San Diego, USA)). The combinations in the different experimental groups are shown in Table 4, below.

TABLE 4

| Group no. | Treatment | No. of animals |
|---|---|---|
| 1 | Untreated control | 5 |
| 2 | anti-PD-1 | 5 |
| 3 | HPV peptide + poly(IC) | 5 |
| 4 | HPV peptide + PCI | 5 |
| 5 | HPV peptide + poly(IC) + PCI | 5 |
| 6 | HPV peptide + anti-PD-1 | 5 |
| 7 | HPV peptide + poly(IC) + anti-PD-1 | 5 |
| 8 | HPV peptide + PCI + anti-PD-1 | 5 |
| 9 | HPV peptide + poly(IC) + PCI + anti-PD-1 | 5 |
| 10 | anti-CTLA4 | 5 |
| 11 | HPV peptide + poly(IC) + PCI + anti-CTLA4 | 5 |
| 12 | HPV peptide + anti-CTLA4 | 2 |

18 hours after each immunisation illumination was performed for 6 minutes, using the LumiSource illumination device (PCI Biotech AS).

Tumour sizes were measured two or three times per week by measuring two perpendicular diameters with a digital caliper. Tumour volumes were calculated using the following formula:

$$V = (W^2 \times L)/2$$

where W is the width and L the length diameters of the tumours measured.

Figure 1:
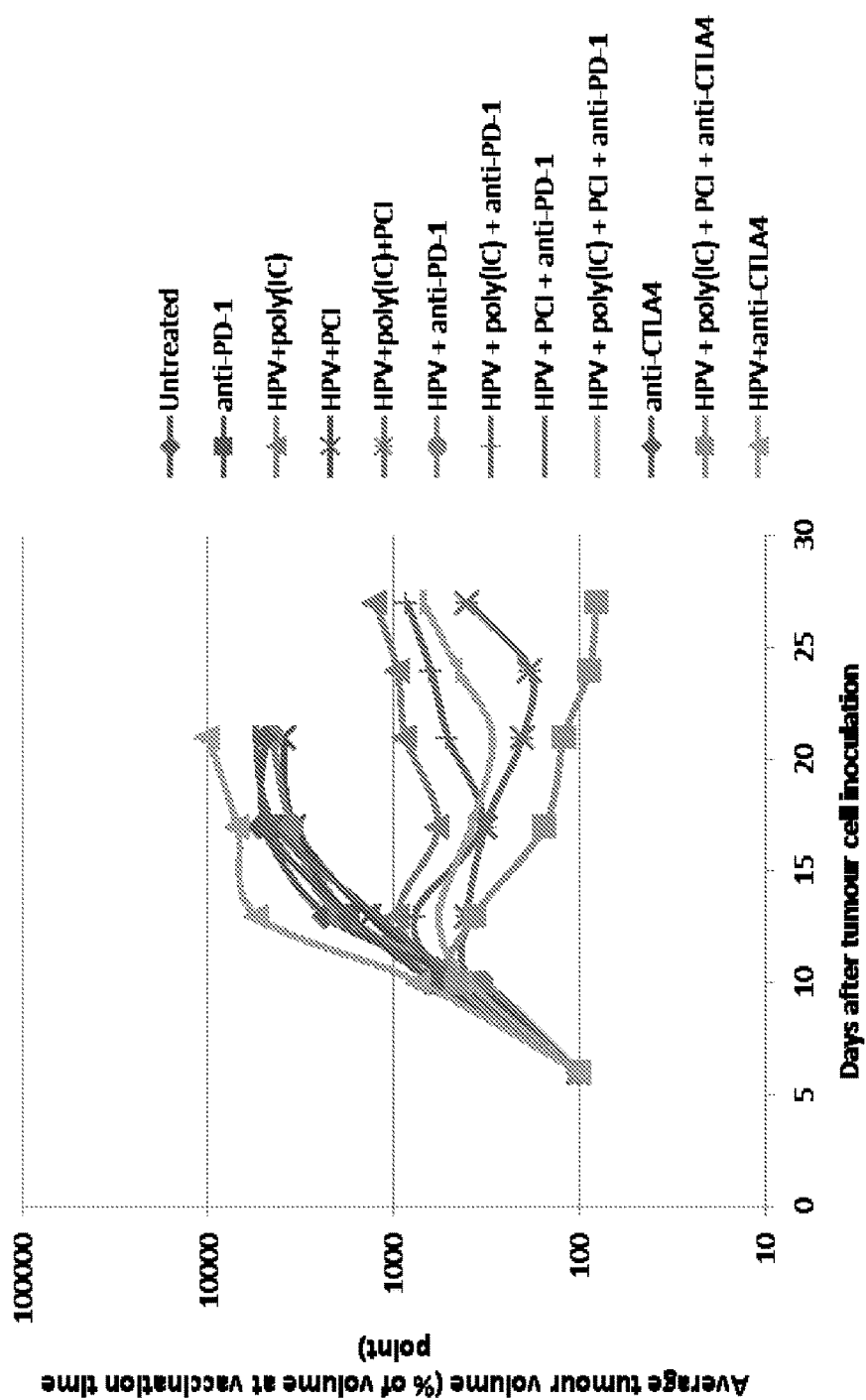
FIG. 1 shows the effect of PCI with the checkpoint inhibitors anti-CTLA4 and anti-PD-1 in the TC-1 mouse model for HPV-induced cancer. The results show average tumour volume as a % of volume at the vaccination time point.

The results are shown in FIG. 1, which shows a reduction in tumour volume in groups in which a checkpoint inhibitor was administered with Poly(IC), HPV and PCI.

Example 2

Materials and Methods

C57BL/6 mice, TPCS$_{2a}$ and Poly(IC) were as described in Example 1. The TRP-2 peptide (sequence SVYDFFVWL) was obtained from United Peptides (Herndon, Va.).

Intradermal Photosensitisation and Immunisation of Normal Mice.

The mice were shaved on the abdominal area (3-4 cm$^2$) and immunised at day 0, day 14 and day 35 with 200 µg of TRP-2 peptide, 100 µg TPCS$_{2a}$ and 10 µg high molecular weight poly(IC) as specified below by intradermal injection using 0.3 ml BD Micro-Fine™+insulin syringes with 30G needles (BD, N.J., USA). The vaccines were kept light protected and used within 60 minutes of preparation. The vaccines were given in two injections of 50 µl each, on the left and right side of the abdominal mid line. At a specified time point after vaccine injection the mice were anaesthetised by subcutaneous injection of a mixture of Zoletil (10 mg/kg body weight, Virbac, Norway) and illuminated where relevant. In some experimental groups (see below) anti-CTLA4 (3 mg/kg, intraperitoneal administration) was administered just before each immunisation.

Illumination of Immunised Mice

Illumination/of the vaccination site with LumiSource (PCI Biotech) was performed for 6 min, 18 hours after immunisation.

Analysis of Immune Responses by Pentamer Staining and Intracellular Staining

On day 60 after the first immunisation the animals were sacrificed, the spleens were removed and the spleen cells were re-stimulated with the TRP-2 peptides and subsequently analysed with intracellular staining for interferon-gamma (IFN-gamma) and tumour necrosis factor alpha (TNF-alpha). Intracellular staining for IFN-γ was performed after overnight stimulation of splenocytes in 24-well plates with the TRP-2 peptides at 37° C. Brefeldin A was added during the last 4 hours. The cells were then washed and fixed with 4% formaldehyde in PBS for 10 min on ice. Anti-CD16/32 was added to block unspecific binding to Fc receptors. The cells were then permeabilised with 0.1% NP40 in PBS for 3 min and washed before staining with anti-IFN-γ, anti-CD8 and ant-CD44 antibodies (eBioscience or BD Pharmingen). The cells were acquired using FACSCanto (BD Biosciences, San Jose, USA) and analysed using FlowJo 8.5.2 software (Tree Star, Inc., Ashland, Oreg.). Intracellular staining for tumour necrosis factor alpha (TNF-alpha) was performed as described for IFN-gamma using anti-TNF-alpha antibodies.

The following experimental groups were included:
1. Untreated Mice were not immunised or illuminated.
2. TRP-2: Mice were immunised with TRP-2 peptide in all immunisations. They were not illuminated.
3. TRP-2+poly(IC): Mice were immunised with TRP-2 peptide and 10 µg poly(IC). They were not illuminated.
4. TRP-2+PCI: Mice were immunised with TRP-2 peptide and 100 µg TPCS$_{2a}$ and illuminated.
5. TRP-2+poly(IC)+PCI: Mice were immunised with TRP-2 peptide, 10 µg poly(IC) and 100 µg TPCS$_{2a}$ and illuminated.
6. TRP-2+poly(IC)+PCI+anti-CTLA4: Mice were immunised with TRP-2 peptide, 10 µg poly(IC), 100 µg TPCS$_{2a}$. Anti-CTLA4 (3 mg/kg, intraperitoneal administration) was administered just before each immunisation. The animals were illuminated.
7. TRP-2+poly(IC)+anti-CTLA4: Mice were immunised with TRP-2 peptide and 10 µg poly(IC). Anti-CTLA4 (3 mg/kg, intraperitoneal administration) was administered just before each immunisation. The animals were not illuminated.

Figure 2:
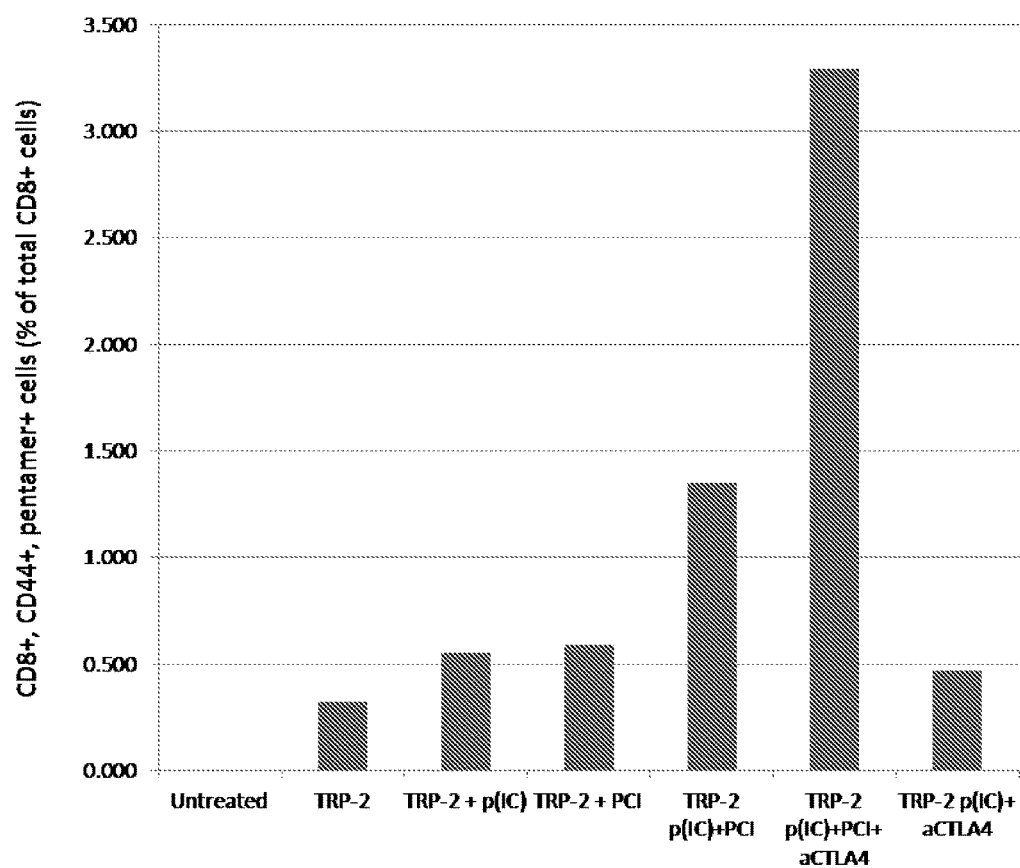
FIG. 2 shows the median values (% antigen-specific, CD44+ cells of the total CD8+ cells) for TRP-2 pentamer staining after re-stimulation of spleen cells (isolated from mice after in vivo treatment as indicated) with the TRP-2 peptide.

FIG. 2 shows the median values (% antigen-specific, CD44+ cells of the total CD8+ cells) for TRP-2 pentamer staining after re-stimulation of spleen cells with the TRP-2 peptide. It can be seen that when the TRP-2 antigen was used with poly(IC) alone (group 3) or with PCI alone (group 4) a significant, but small increase in antigen-specific cells were observed over what was seen with antigen alone (group 2). The addition of anti-CTLA4 to the TRP-2 peptide+poly(IC) combination (group 7) did not seem to increase the response over what was seen with TRP-2 peptide+poly(IC). Combining TRP-2 peptide+poly(IC) with PCI clearly enhanced the immunological response (group 5), and adding anti-CTLA4 to this combination increased the response more than two times further, showing a synergistic effect of PCI and anti-CTLA4 on the proliferation of antigen specific CD8+, CD44+ T-cells in this experimental system.

Figure 3:
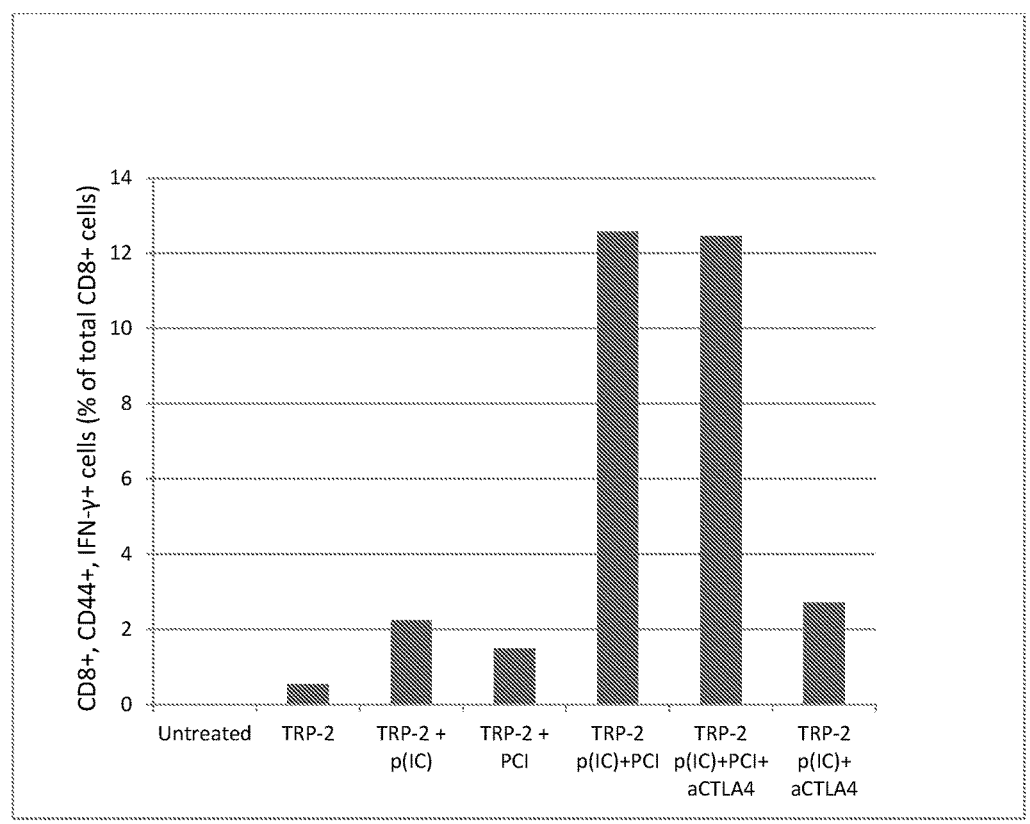
FIG. 3 shows the results from interferon-gamma (IFN-gamma) intracellular staining after re-stimulation of spleen cells (isolated from mice after in vivo treatment as indicated) with the TRP-2 peptide.

FIG. 3 shows the results from interferon-gamma (IFN-gamma) intracellular staining after re-stimulation of spleen cells with the TRP-2 peptide. For this marker the combination of anti-CTLA4 with PCI and poly(IC) did not seem increase the marker expression over what was seen with the PCI+poly(IC) combination.

Figure 4:
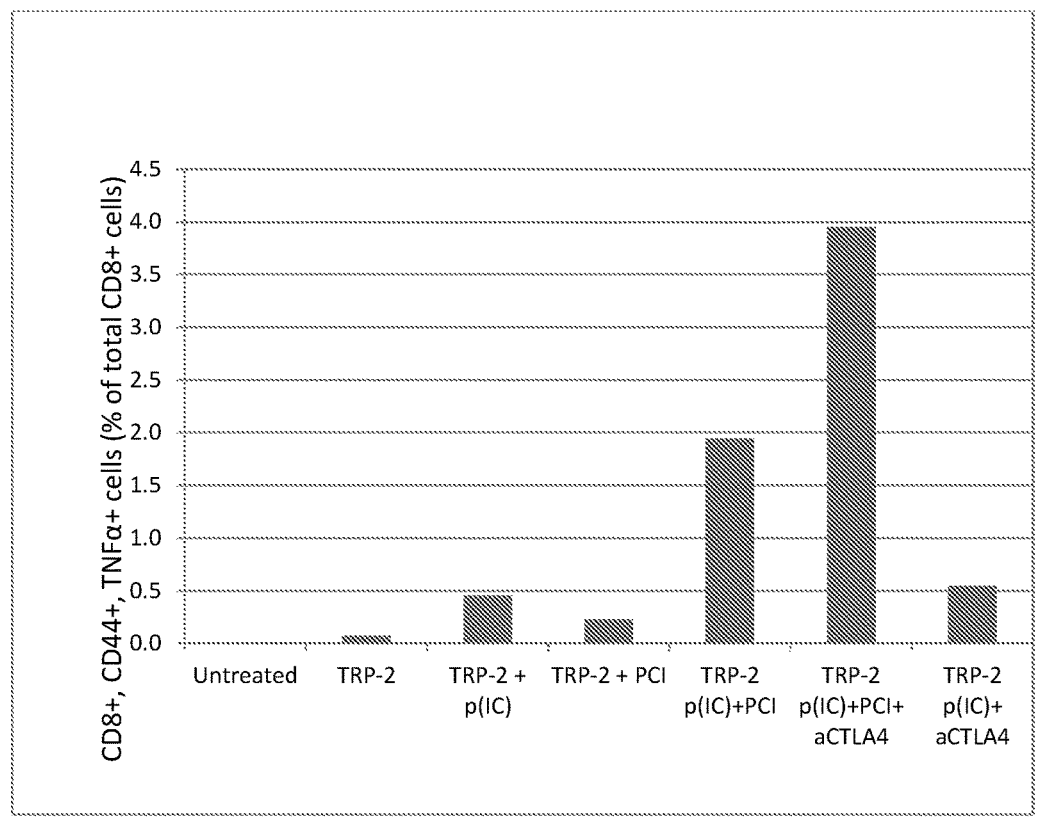
FIG. 4 shows the results from TNF-alpha intracellular staining after re-stimulation of spleen cells (isolated from mice after in vivo treatment as indicated) with the TRP-2 peptide.

FIG. 4 shows the results from TNF-alpha intracellular staining after re-stimulation of spleen cells with the TRP-2 peptide. In accordance with the results shown in FIG. 2 it can be seen that the addition of anti-CTLA4 to the TRP-2 peptide+poly(IC) combination (group 7) did not seem to increase the response over what was seen with TRP-2 peptide+poly(IC) (group 3). However adding anti-CTLA4 to the TRP-2 peptide+poly(IC)+PCI combination significantly increased the TNF-alpha expression response, showing a synergistic effect of PCI and anti-CTLA4 on antigen induced TNF-alpha expression in CD8+, CD44+ T-cells in this experimental system.

Example 3

The study was performed to investigate the effect of PCI vaccination in combination with the checkpoint inhibitors anti-CTLA4 and anti-PD-1 (used together) in the TC-1 mouse model for HPV-induced cancer.

Materials and Methods

Mice were as described in Example 1. Mice were inoculated subcutaneously on their right flank with 100,000 TC-1 tumour cells (licensed from The Johns Hopkins University, 3400 N. Charles St., Baltimore, Md. 21218-2695) on day 0.

Checkpoint inhibitors anti-CTLA4 and anti-PD-1, photosensitizing agent TPCS$_{2a}$, and HPV long peptide antigen were as described in Example 1.

Immunisation Protocol

The treatment schedule is outlined in Table 5.

TABLE 5

Treatment schedule

| Day | | Checkpoint inhibitor administration (i.p.) |
|---|---|---|
| 0 | Tumour inoculation | |
| 4 | | x |
| 7 | 1st immunisation | x |
| 8 | 1st illumination | |
| 11 | | x |
| 14 | 2nd immunisation | x |
| 15 | 2nd illumination | |
| 18 | | x |
| 21 | 3rd immunisation | x |
| 22 | 3rd illumination | |
| 25 | | x |

The PCI treated animals were illuminated 18 hours after each immunization. Illumination was performed for 6 min, using the LumiSource illumination device (PCI Biotech AS). The checkpoint inhibitors anti-CTLA4 and anti-PD-1 were administered together by intraperitoneal injection at the time points shown in Table 5. The doses of the checkpoint inhibitors were 100 µg per injection for anti-CTLA4, and 200 µg for anti-PD-1. Tumour sizes were measured two or three times per week by measuring two perpendicular diameters with a digital caliper. Tumour volumes were calculated as described in Example 1.

The combinations used in the different experimental groups are shown in Table 6.

TABLE 6

Experimental Groups

| Group no. | Treatment | No. of animals |
|---|---|---|
| 1 | Untreated | 5 |
| 2 | anti-PD-1/antiCTLA4 (i.p.) | 5 |
| 3 | HPV peptide (i.d.) + anti-PD-1/antiCTLA4 (i.p.) | 5 |
| 4 | HPV peptide + PCI (i.d.) anti-PD-1/antiCTLA4 (i.p.) | 5 |

Figure 5:
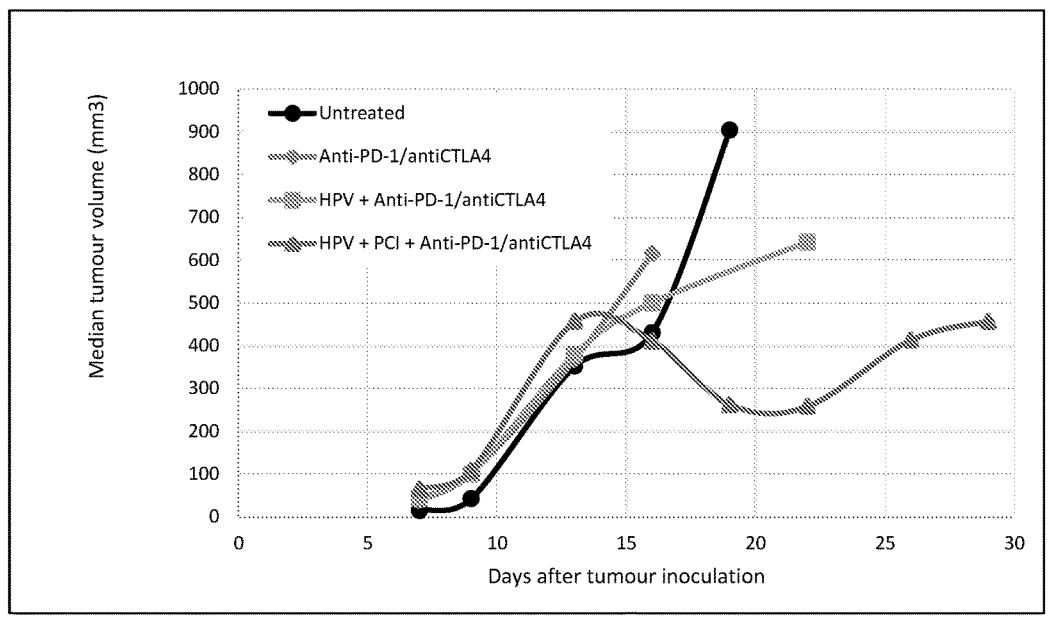
FIG. 5 shows the effect of PCI with the checkpoint inhibitors anti-CTLA4 and anti-PD-1 (used together) in the TC-1 mouse model for HPV-induced cancer. The results show median tumour volume after tumour inoculation.
Figure 6:
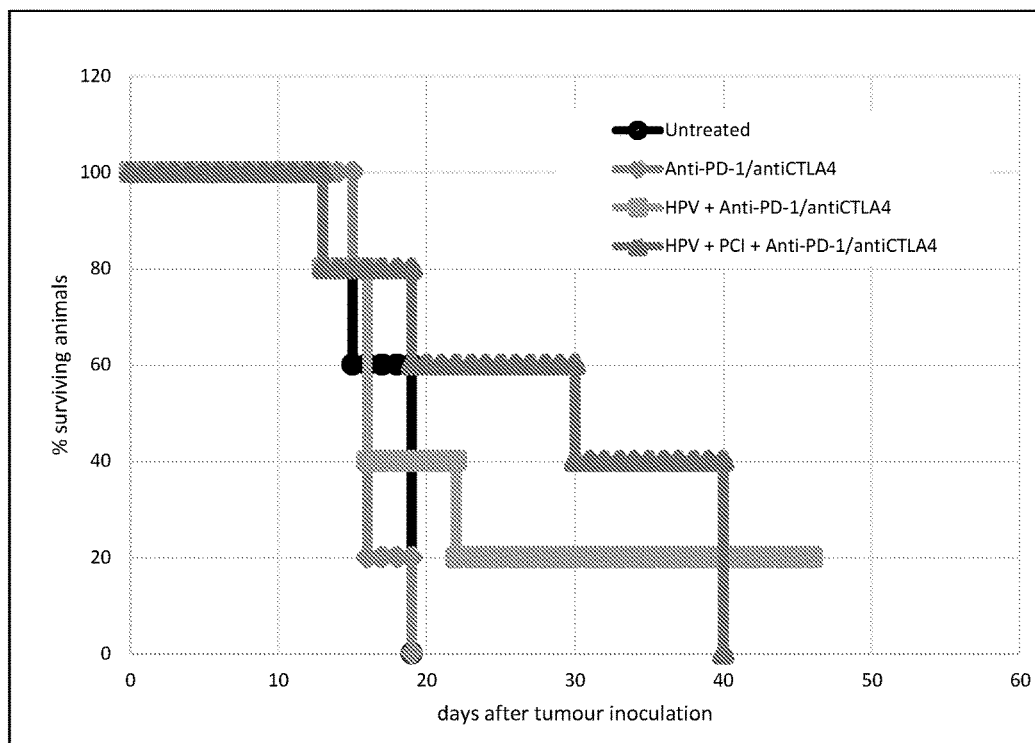
FIG. 6 shows the effect of PCI with the checkpoint inhibitors anti-CTLA4 and anti-PD-1 (used together) in the TC-1 mouse model for HPV-induced cancer. The results show animal survival after tumour inoculation.

The results are shown in FIG. 5 from which it can be seen that administering the combination of the checkpoint inhibitors anti-CTLA4 and anti-PD-1 had little effect on tumour growth, even if these inhibitors were combined with the HPV long peptide antigen, expressed by the tumour. However, if PCI was added to the treatment regimen with the checkpoint inhibitors a significant inhibition of tumour growth was observed. Thus, a clear tumour shrinkage was induced, with an onset about one week after the initial PCI treatment, indicating a PCI-induced immunologically mediated anti-tumour effect. The effect of PCI also translated into an improved survival of the animals, as can be seen from FIG. 6.

Example 4

The study was performed to investigate the effect of PCI vaccination in combination with the checkpoint inhibitors anti-CTLA4 and anti-PD-1 (used together) and TLR ligand poly(IC) in the TC-1 mouse model for HPV-induced cancer.

Materials and Methods

Mice were inoculated with TC-1 tumour cells as described in Example 3. Checkpoint inhibitors anti-CTLA4 and anti-PD-1, photosensitizing agent $TPCS_{2a}$, HPV long peptide antigen and Poly(IC) were as described in Example 1.

Immunisation Protocol

The treatment schedule is outlined in Table 7.

TABLE 7

Treatment schedule

| Day | | Checkpoint inhibitor administration (i.p.) |
|---|---|---|
| 0 | Tumour inoculation | |
| 4 | | x |
| 7 | 1st immunisation | x |
| 8 | 1st illumination | |
| 11 | | x |
| 14 | 2nd immunisation | x |
| 15 | 2nd illumination | |
| 18 | | x |
| 21 | 3rd immunisation | x |
| 22 | 3rd illumination | |
| 25 | | x |

Each immunisation was performed by intradermal administration of a mixture consisting of different combinations of 50 µg HPV long peptide antigen, 25 µg $TPCS_{2a}$ (for the animals receiving PCI treatment) and 5 µg poly(IC). The PCI treated animals were illuminated 18 hours after each immunization. Illumination was performed for 6 min, using the LumiSource illumination device (PCI Biotech AS). The checkpoint inhibitors anti-CTLA4 and anti-PD-1 were administered together by intraperitoneal injection at the time points shown in Table 7. The doses of the checkpoint inhibitors were 100 µg per injection for anti-CTLA4, and 200 µg for anti-PD-1. Tumour sizes were measured as described in Example 1.

The combinations used in the different experimental groups are shown in Table 8.

TABLE 8

Experimental Groups

| Group no. | Treatment | No. of animals |
|---|---|---|
| 1 | Untreated | 5 |
| 2 | anti-PD-1/antiCTLA4 (i.p.) | 5 |
| 3 | HPV peptide + poly(IC) (i.d.) + anti-PD-1/antiCTLA4 (i.p.) | 5 |
| 4 | HPV peptide + poly(IC) + PCI (i.d.) + anti-PD-1/antiCTLA4 (i.p.) | 5 |
| 5 | HPV peptide + poly(IC) + PCI (i.d.) | 5 |

Figure 7:
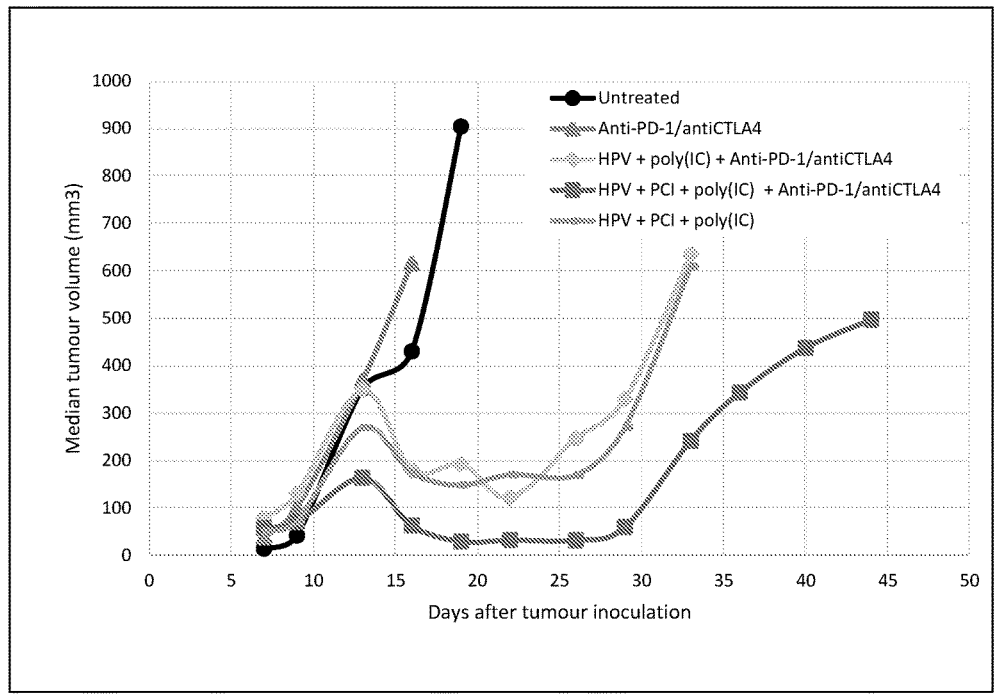
FIG. 7 shows the effect of PCI with the checkpoint inhibitors anti-CTLA4 and anti-PD-1 (used together) when used in conjunction with poly(IC) in the TC-1 mouse model for HPV-induced cancer. The results show median tumour volume after tumour inoculation.
Figure 8:
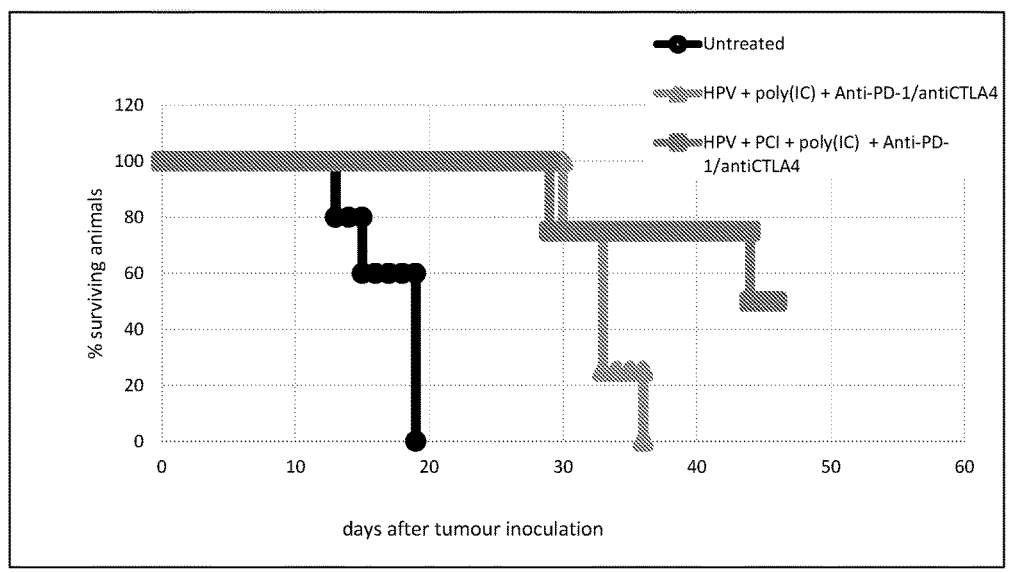
FIG. 8 shows the effect of PCI with the checkpoint inhibitors anti-CTLA4 and anti-PD-1 (used together) when used in conjunction with poly(IC) in the TC-1 mouse model for HPV-induced cancer. The results show animal survival after tumour inoculation.

The results are shown in FIG. 7 from which it can be seen that administering the TLR3 ligand poly(IC) in addition to the combination of the check point inhibitors anti-CTLA4 and anti-PD-1 had a significant inhibitory effect on the tumour growth. When PCI was added to this treatment a strongly increased anti-tumour effect was observed, with the median tumour volume shrinking to a size below the size at the start of the experiment, and the shrinkage lasting for at least two weeks. The effect of PCI also translated into a strongly improved survival of the animals as can be seen from FIG. 8.

Example 5

The study was performed to investigate the effect of PCI vaccination in combination with the checkpoint inhibitor anti-PD-1 in the TC-1 mouse model for HPV-induced cancer.

Materials and Methods

Mice were inoculated with TC-1 tumour cells as described in Example 3. Checkpoint inhibitor anti-PD-1, photosensitizing agent $TPCS_{2a}$ and HPV long peptide antigen were as described in Example 1.

Immunisation Protocol

The treatment schedule is outlined in Table 9.

TABLE 9

Treatment Schedule

| Day | | Anti-PD-1 administration (i.p.) |
|---|---|---|
| 0 | Tumour inoculation | |
| 4 | | x |
| 7 | 1st immunisation | x |
| 8 | 1st illumination | |
| 11 | | x |
| 14 | 2nd immunisation | x |
| 15 | 2nd illumination | |
| 18 | | x |
| 21 | 3rd immunisation | x |
| 22 | 3rd illumination | |
| 25 | | x |
| 28 | 4th immunisation | x |
| 29 | 4th illumination | |
| 32 | | x |
| 36 | | x |

Each immunisation was performed by intradermal administration of a mixture consisting of different combinations of 50 µg HPV long peptide antigen and 25 µg $TPCS_{2a}$ (for the animals receiving PCI treatment). The PCI treated animals were illuminated 18 hours after each immunization. Illumination was performed for 6 min, using the LumiSource illumination device (PCI Biotech AS). 200 µg of the checkpoint inhibitor anti-PD-1 was administered by intraperitoneal injection at the time points shown in Table 9. Tumour sizes were measured as described in Example 1.

The combinations used in the different experimental groups are shown in Table 10.

TABLE 10

Experimental Groups

| Group no. | Treatment | No. of animals |
|---|---|---|
| 1 | Untreated | 5 |
| 2 | HPV (i.d.) + anti-PD-1 (i.p.) | 8 |
| 3 | HPV (i.d.) + anti-PD-1 (i.p.) + PCI | 8 |

Figure 9:
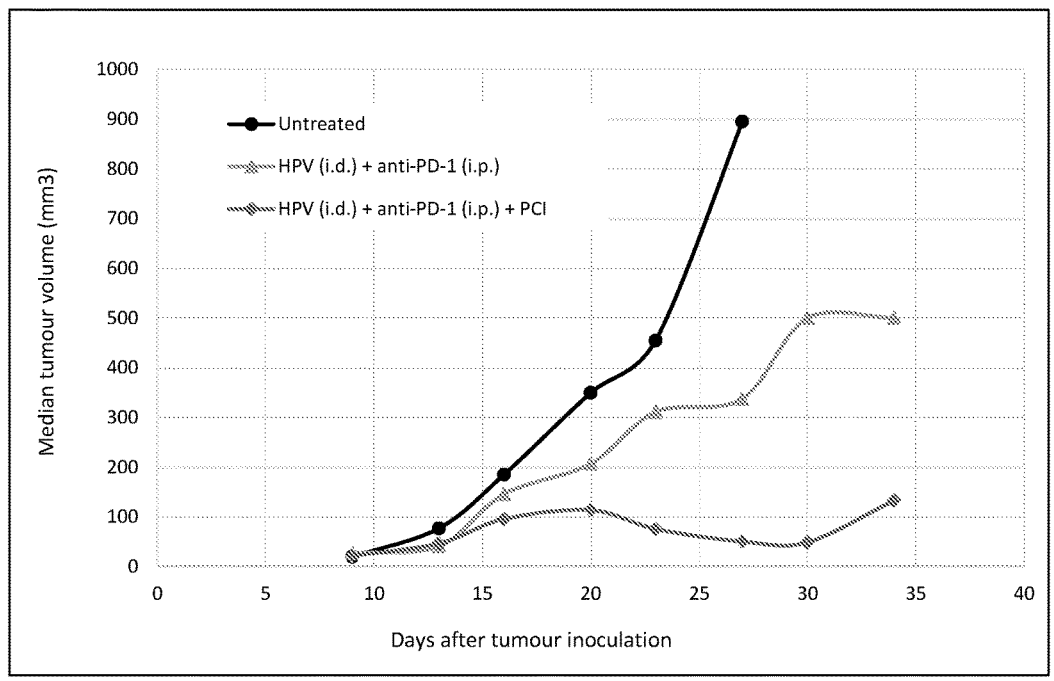
FIG. 9 shows the effect of PCI with the checkpoint inhibitor anti-PD-1 in the TC-1 mouse model for HPV-induced cancer. The results show median tumour volume after tumour inoculation.
Figure 10:
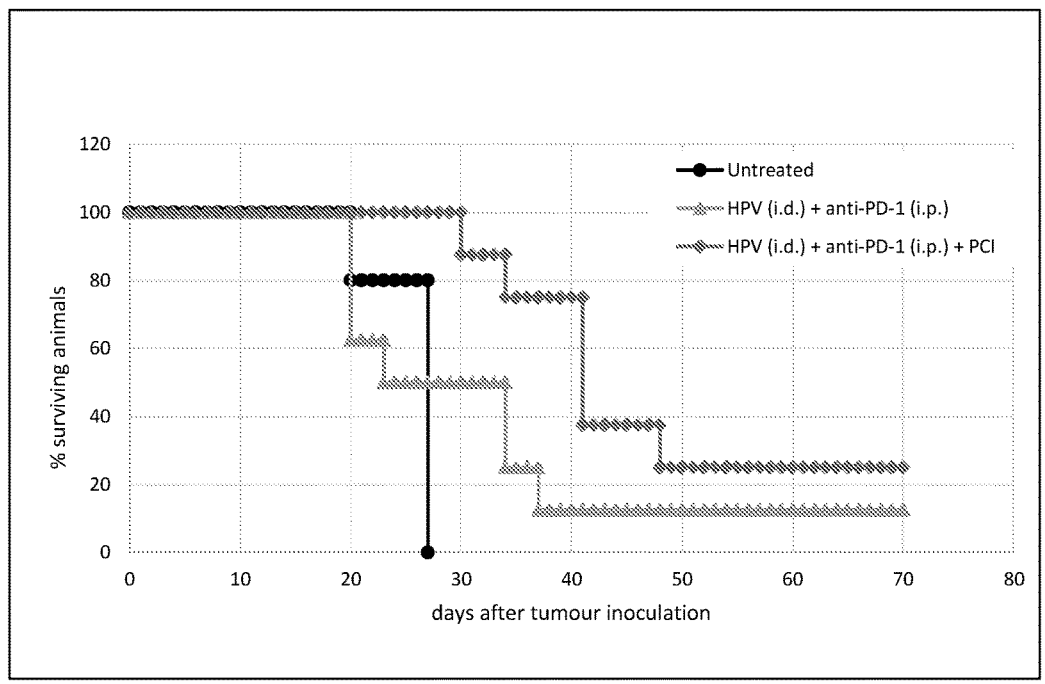
FIG. 10 shows the effect of PCI with the checkpoint inhibitor anti-PD-1 in the TC-1 mouse model for HPV-induced cancer. The results show animal survival after tumour inoculation.
Figure 11:
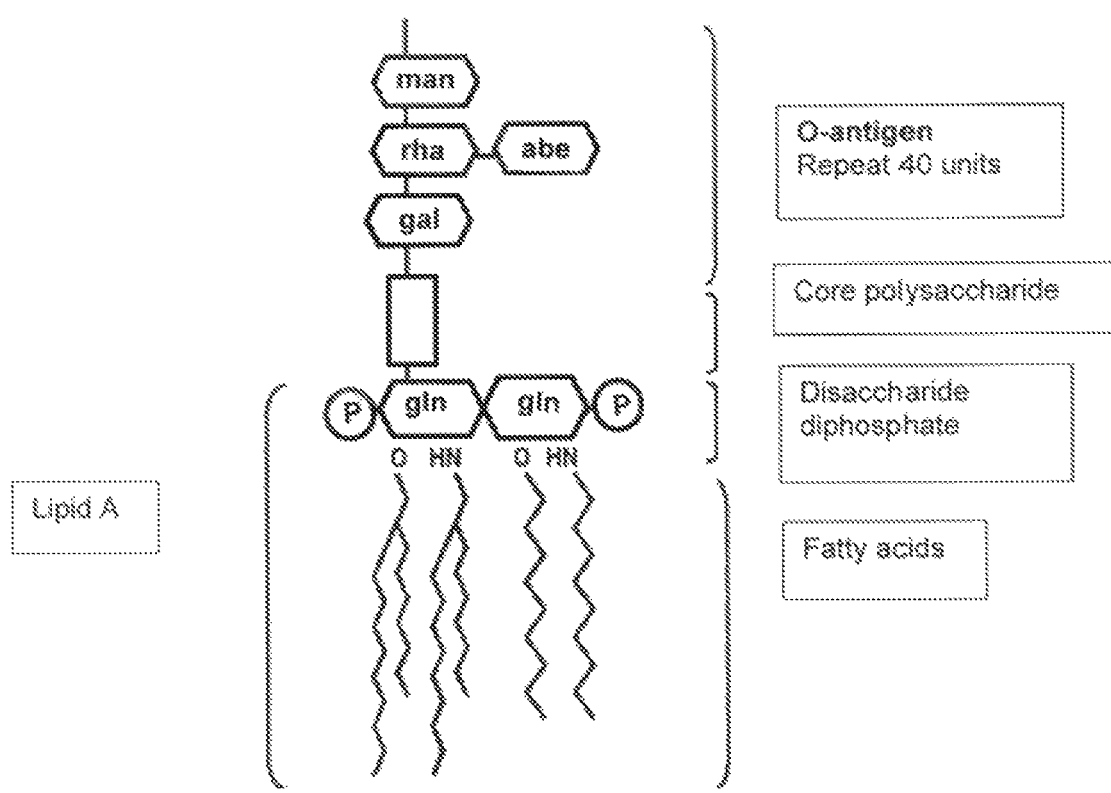
FIG. 11 shows the structure of a lipopolysaccharide.

The results are shown in FIG. 9 from which it can be seen that administering the checkpoint inhibitor anti-PD-1 together with the HPV peptide antigen had a small inhibitory effect on tumour growth. However, if PCI was added to this treatment regimen a significant increase in the inhibition of tumour growth was achieved. Thus, a clear tumour shrinkage was observed, something that was not seen with the checkpoint inhibitor (+antigen) alone. The effect of PCI also translated into an improved survival of the animals, as can be seen from FIG. 10.

The invention claimed is:

1. A method of generating an immune response in a subject, comprising administering to a subject an antigenic molecule, a photosensitizing agent, a checkpoint inhibitor and a TLR3 ligand, and irradiating said subject with light of a wavelength effective to activate said photosensitizing agent, wherein an immune response is thereby generated, wherein
   the antigenic molecule is a peptide,
   the checkpoint inhibitor is an anti-CTLA4 antibody, an anti-PD-1 antibody, or both an anti-CTLA4 antibody and an anti-PD-1 antibody, and
   the TLR3 ligand is a double stranded RNA molecule.

2. The method as claimed in claim 1 wherein the checkpoint inhibitor is a monoclonal antibody.

3. The method as claimed in claim 1 wherein the checkpoint inhibitor is (i) an anti-CTLA4 antibody and an anti-PD-1 antibody or (ii) an anti-CTLA4 antibody.

4. The method as claimed in claim 1 wherein said double stranded RNA molecule is Poly(I:C).

5. The method as claimed in claim 1 wherein the antigenic molecule is a molecule capable of stimulating an immune response, preferably a vaccine antigen or vaccine component and preferably comprises more than one antigen.

6. The method as claimed in claim 1 wherein the photosensitising agent is selected from $TPCS_{2a}$, $AlPcS_{2a}$, $TPPS_4$ and $TPBS_{2a}$, preferably $TPCS_{2a}$.

7. The method as claimed in claim 1 wherein the antigenic molecule is a melanoma peptide or Human Papillomavirus (HPV) peptide.

8. The method as claimed in claim 1 wherein said method is a method of vaccination.

9. The method as claimed in claim 1 wherein a disease, disorder or infection is treated or prevented when said immune response is generated, and wherein said disease, disorder or infection is preferably cancer, preferably melanoma or a cancer associated with a papillomavirus.

10. The method as claimed in claim 1 wherein said subject is a mammal, preferably a cat, dog, horse, donkey, sheep, pig, goat, cow, mouse, rat, rabbit or guinea pig, most preferably the subject is a human.

11. The method as claimed in claim 1 wherein said antigenic molecule, photosensitising agent, checkpoint inhibitor and TLR3 ligand are administered to said subject simultaneously, separately or sequentially.

* * * * *

SEQUENCE LISTING

```
<160> NUMBER OF SEQ ID NOS: 9

<210> SEQ ID NO 1
<211> LENGTH: 35
<212> TYPE: PRT
<213> ORGANISM: Human papillomavirus type 16

<400> SEQUENCE: 1

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 2
<211> LENGTH: 9
<212> TYPE: PRT
<213> ORGANISM: Human papillomavirus type 16

<400> SEQUENCE: 2

Arg Ala His Tyr Asn Ile Val Thr Phe
1               5

<210> SEQ ID NO 3
<211> LENGTH: 10
<212> TYPE: PRT
<213> ORGANISM: Artificial Sequence
<220> FEATURE:
<223> OTHER INFORMATION: FSL-1 Sequence
<220> FEATURE:
<221> NAME/KEY: Diacylated Cysteine
<222> LOCATION: (1)
<223> OTHER INFORMATION: X = Cys-S-(2,3-bis(palmitoyloxy)propyl)
```

```
<400> SEQUENCE: 3

Xaa Gly Asp Pro Lys His Pro Lys Ser Phe
1               5                   10

<210> SEQ ID NO 4
<211> LENGTH: 20
<212> TYPE: DNA
<213> ORGANISM: Artificial Sequence
<220> FEATURE:
<223> OTHER INFORMATION: ODN 1826
<220> FEATURE:
<221> NAME/KEY: Phosphorothioate Backbone
<222> LOCATION: (1)..(20)

<400> SEQUENCE: 4
tccatgacgt tcctgacgtt                                               20

<210> SEQ ID NO 5
<211> LENGTH: 22
<212> TYPE: DNA
<213> ORGANISM: Artificial Sequence
<220> FEATURE:
<223> OTHER INFORMATION: ODN 2395
<220> FEATURE:
<221> NAME/KEY: Phosphorothioate Backbone
<222> LOCATION: (1)..(22)

<400> SEQUENCE: 5
tcgtcgtttt cggcgcgcgc cg                                            22

<210> SEQ ID NO 6
<211> LENGTH: 12
<212> TYPE: DNA
<213> ORGANISM: Artificial Sequence
<220> FEATURE:
<223> OTHER INFORMATION: Hairpin Sequence

<400> SEQUENCE: 6
cggcgcgcgc cg                                                       12

<210> SEQ ID NO 7
<211> LENGTH: 10
<212> TYPE: RNA
<213> ORGANISM: Staphylococcus aureus

<400> SEQUENCE: 7
cggaaagacc                                                          10

<210> SEQ ID NO 8
<211> LENGTH: 19
<212> TYPE: RNA
<213> ORGANISM: Staphylococcus aureus

<400> SEQUENCE: 8
ggacggaaag accccgugg                                                19

<210> SEQ ID NO 9
<211> LENGTH: 9
<212> TYPE: PRT
<213> ORGANISM: Homo sapiens

<400> SEQUENCE: 9

Ser Val Tyr Asp Phe Phe Val Trp Leu
1               5
```